United States Patent [19]

Markonius

[11] Patent Number: 5,449,794

[45] Date of Patent: Sep. 12, 1995

[54] BENZOPYRAN PHENOL DERIVATIVES FOR USE AS ANTIBACTERIAL AGENTS

[75] Inventor: Maria Markonius, Johanneshov, Sweden

[73] Assignees: Jasmine Fockerman; Michel Fockerman, both of Stockholm, Sweden

[21] Appl. No.: 809,420

[22] Filed: Dec. 17, 1991

Related U.S. Application Data

[63] Continuation-in-part of Ser. No. 656,801, Feb. 15, 1991, abandoned.

[51] Int. Cl.⁶ ............................................ A61K 31/35
[52] U.S. Cl. ..................................................... 514/456
[58] Field of Search ......................................... 514/456

[56] References Cited

U.S. PATENT DOCUMENTS 4,352,792  10/1982  Ishitsuka et al. ..................... 424/180
4,866,080  9/1989   Timar et al. ......................... 514/456

FOREIGN PATENT DOCUMENTS 1057349  2/1967  Germany .
2145082  3/1985  United Kingdom .

OTHER PUBLICATIONS

Metzner et al., Zur antimikrobiellen Wirksamkeit von Propolis und Propolisinhaltsstoffen, Pharmazie 34, H. 2 (1979), pp. 97–102.

Dictionary of Organic Compounds, vol. Two, Fifth Edition, Clos–Dop.

*Primary Examiner*—C. Warren Ivy
*Assistant Examiner*—A. Owens
*Attorney, Agent, or Firm*—Olive & Olive

[57] ABSTRACT

A method of inhibiting microorganisms, including bacteria, using benzopyran phenol derivates from propolis. Propolis is extracted with an alcohol, and the resulting compounds are effective as antibacterial, antiviral or immunostimulating agents.

2 Claims, 45 Drawing Sheets

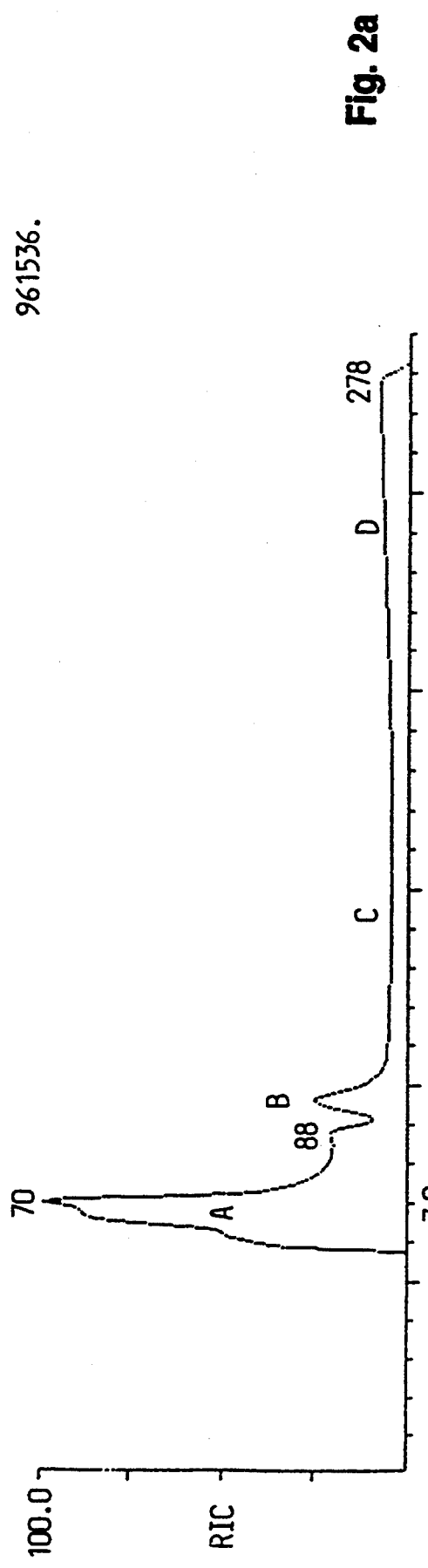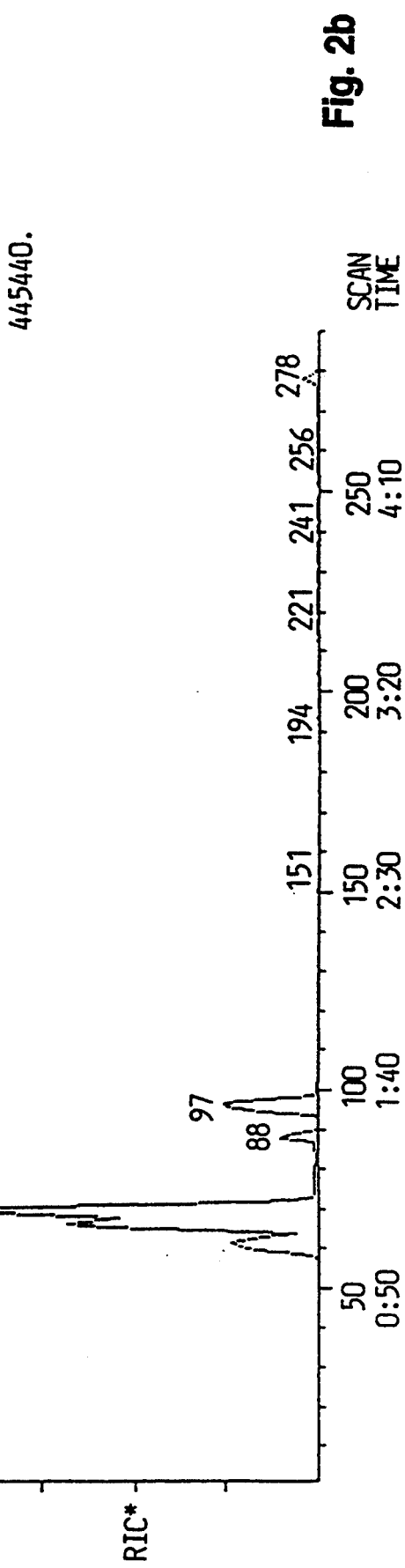

BENZOPYRAN PHENOL DERIVATIVES FOR USE AS ANTIBACTERIAL AGENTS

This application is a CIP of U.S. Ser. No. 07/656,801 filed Feb. 15, 1991 now abandoned.

BACKGROUND OF THE INVENTION

1. Field of the Invention

The present invention concerns benzopyran phenol derivates or mixtures thereof for use as antibacterial, antiviral or immunostimulating agents, a process for preparing a mixture of such derivates and a composition for human or veterinary use containing at least one of these derivates.

2. Description of the Related Art

The benzopyran phenol derivates according to the invention can be derived from propolis. The ethanol extract of propolis can be used as prophylaxis against inflammations caused by certain viral infections (influenza, herpes) and is used as an inflammatory agent.

Propoils, also known as bee glue, is a natural product of bees. Bees collect propolis on the buds and other parts of plants, using it in their habitat to block up holes and cracks and to isolated foreign bodies (insects and other living creatures) in the hive, thus preventing the spread of infections. It is also used by the bees to coat the cells of the honeycomb before storing their products such as honey and pollen in the honeycomb cells.

Propolis is a specific complex bioactive substance consisting of more than 60 compounds. The basis components are different resins, waxes, ethereal oils, ethereal oils and pollen. In addition, major bioactive ingredients of propolis are vegetable dyes, of which the most important are the flavones or yellow dyes such as chrysin or tectochrysin, flavonones such as pinostrombin, and quercetin and their derivatives, and also flavonols such as rhamnocitrin, galangin and isoalpinin. It also contains aromatic substances such as isovanillin and acetoxybetulinol, and aromatic acids such as cinnamic acid, benzoic acid, caffeic acid, ferulic acid and protacatechuic acid with their esters with benzyl alcohol, pentanol phenylethyl alcohol and cinnamyl alcohol (E. M. Schneidewind, A. Brige, H. Kala, J. Metzner, and A. Zsunke, in Die Pharmazie No. 34, 1979, 103). Some substances listed may exert an antimicrobial and fungistatic effect; however, neither pinocembrin nor pinobanksin-3-acetate had been known to be present in propolis, nor have they been shown to have the activity according to the invention herein.

SUMMARY OF THE INVENTION

Compounds of the general formula I

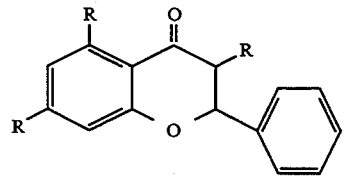

in which R is the same or different and represents either H, OH or

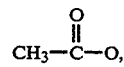

are components in propolis that can be used as antibacterial, antiviral or immunostimulating agents, which agents have better effects than propolis.

The invention especially concerns the use of pinocembrin (4H-1-benzopyran-4-one, 2,3-dihydro-5,7-dihydroxy-2-phenyl) and pinobanksin-3-acetate (4H-1-benzopyran-4-one, 2,3-dihydro-5,7-dihydroxy-2-phenyl-3-acetate) for use as an antibacterial, antiviral or immunostimulating agent.

The invention also concerns mixtures of compounds with the general formula I and especially mixtures of pinocembrin and pinobanksin-3-acetate. Preferably the two compounds are used together in the treatment. The extract containing pinocembrin and pinobanksin-3-acetate is called Propinocom, shortened to PRP-C.

Other aspects and features of the invention will be more fully apparent from the following disclosure and appended claims.

DATA:XTRN020408 #245; BASE M/Z:169; CALI: CALI910204Q1 #2; RIC:59968.

Figure 1A:
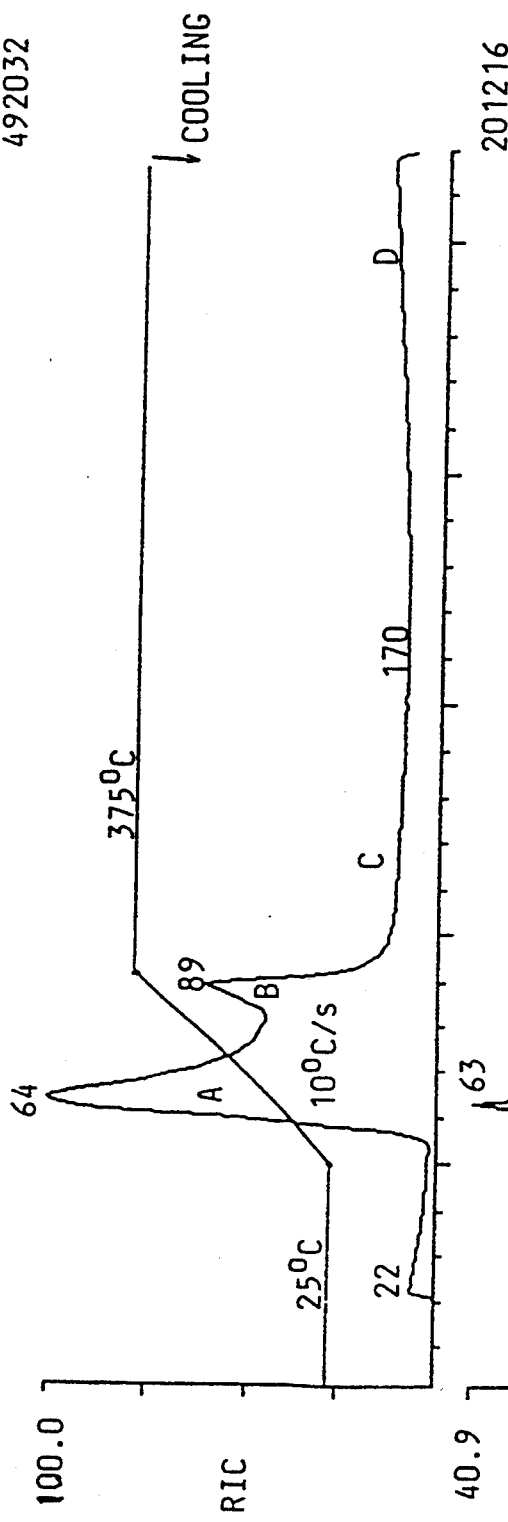
FIG. 1a shows the mass spectra of the dialyzed product including the temperature ramp, the four regions A–D and the total ion stream.
Figure 1B:
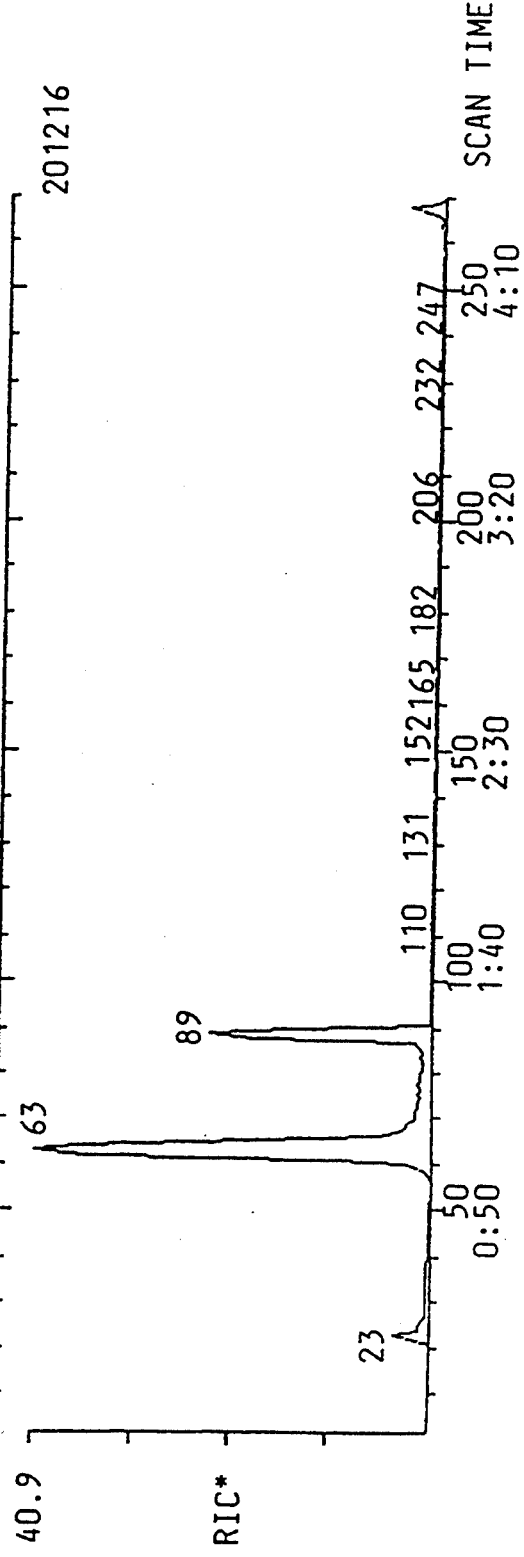
FIG. 1b shows the total ion stream after a numerical filter. Chromatogram information for FIGS. 1a and 1b is RIC; Feb. 04, 1991 15:39:00; SAMPLE: PROV D(50%D); CONDS: +/EI/Q1 MASS SPECTRUM/GAIN:7/EM1200/IS150/EV70/SOLID; RANGE: G 1, 296; LABEL: N O, 4.0; BASE: U20, 3; DATA: XTRN020408 #1, XTRNO20408$; CALI: CAL910204q1 #2, CAL910204Q1 #4847; SCANS 1–270.
Figure 1C:
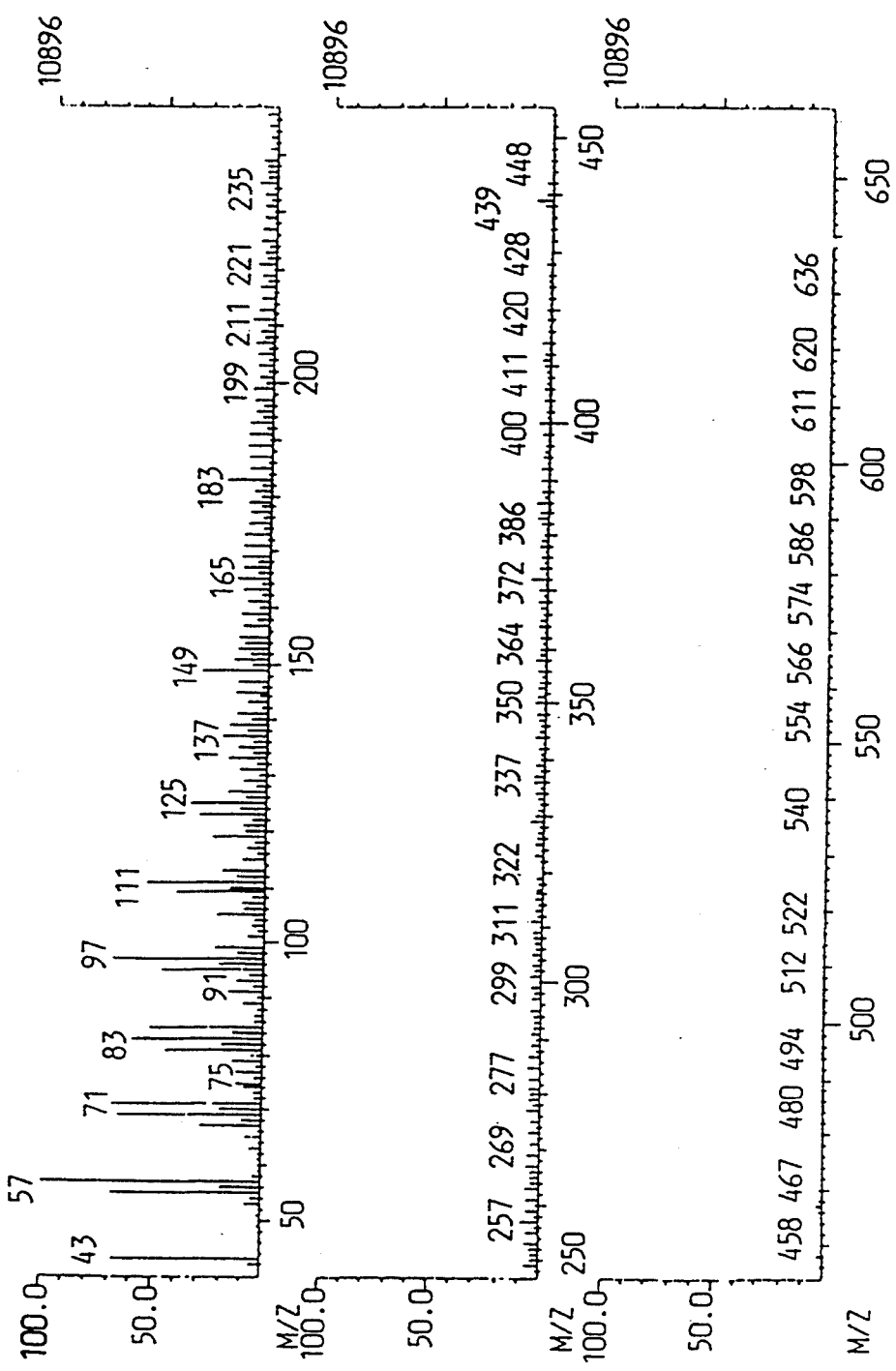
FIG. 1c shows the spectrum in the region A of FIG. 1a. Chromatogram information for FIG. 1c is MASS SPECTRUM; Feb. 04, 1991 15:39:00+1:05; SAMPLE: PROV D (50%D); CONDS.: +/EI/Q1MASS SPECTRUM/GAIN:7/EM1200/IS150/EV70/SOLID; GC TEMP: 45 DEG. C; #60 TO #70 AVERAGED −#85 TO #90 −#41 TO #58 X1.00; DATA:XTRN020408 #65; BASE M/Z:57; CALI: CALI910204Q1 #2.
Figure 1D:
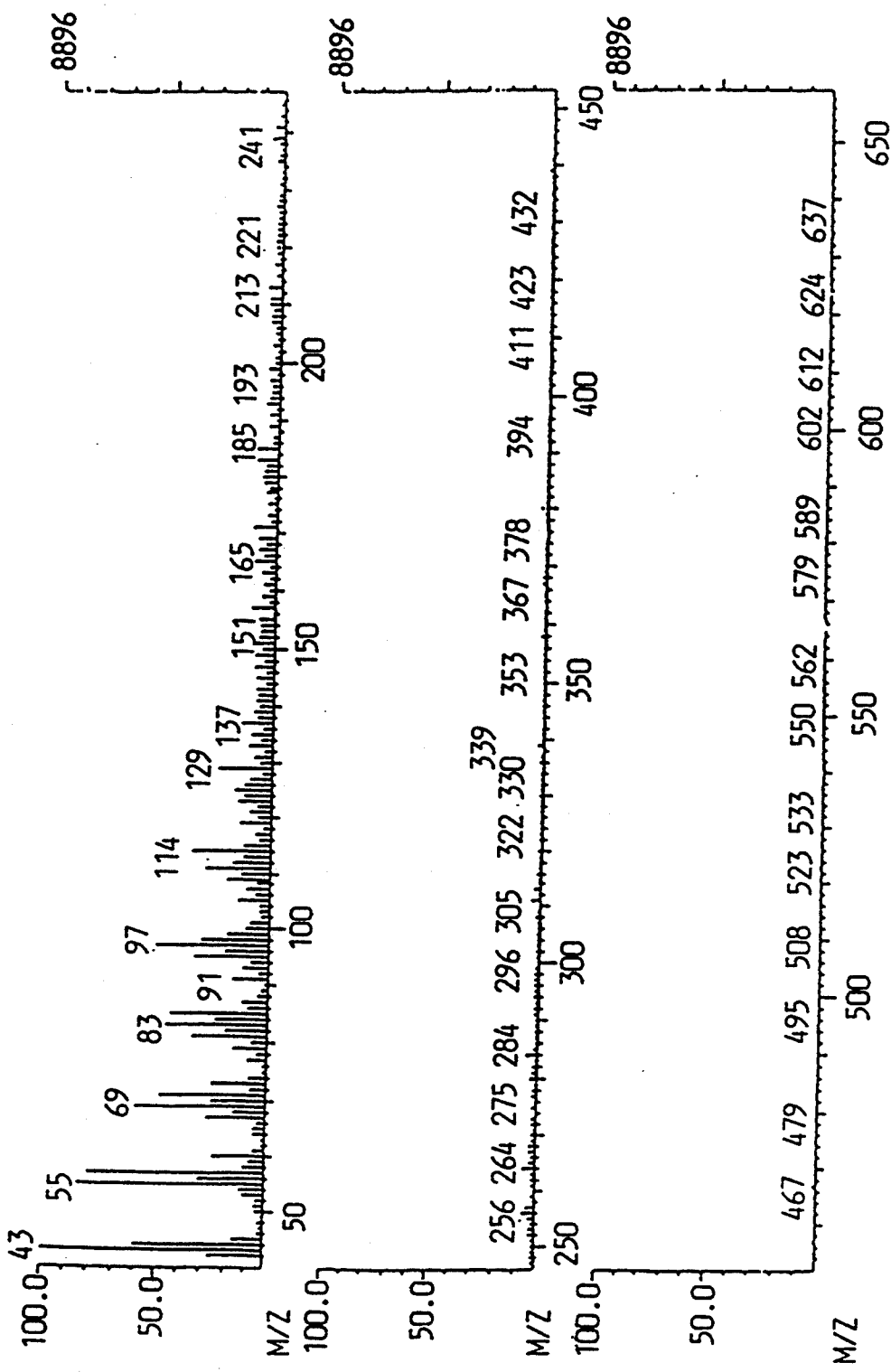
FIG. 1d shows the spectrum of region B of FIG. 1a. Chromatogram information for FIG. 1d is MASS SPECTRUM; Feb. 04, 1991 15:39:00+1:28; SAMPLE: PROV D (50%D); CONDS.: +/EI/Q1MASS SPECTRUM/GAIN:7/EM1200/IS150/EV70/SOLID; GC TEMP: 45 DEG. C; #86 TO #90 AVERAGED −#100 TO #110 −#51 TO #59 X1.00; DATA:XTRN020408 #88; BASE M/Z:43; CALI: CALI910204Q1 #2; RIC:206592.
Figure 1E:
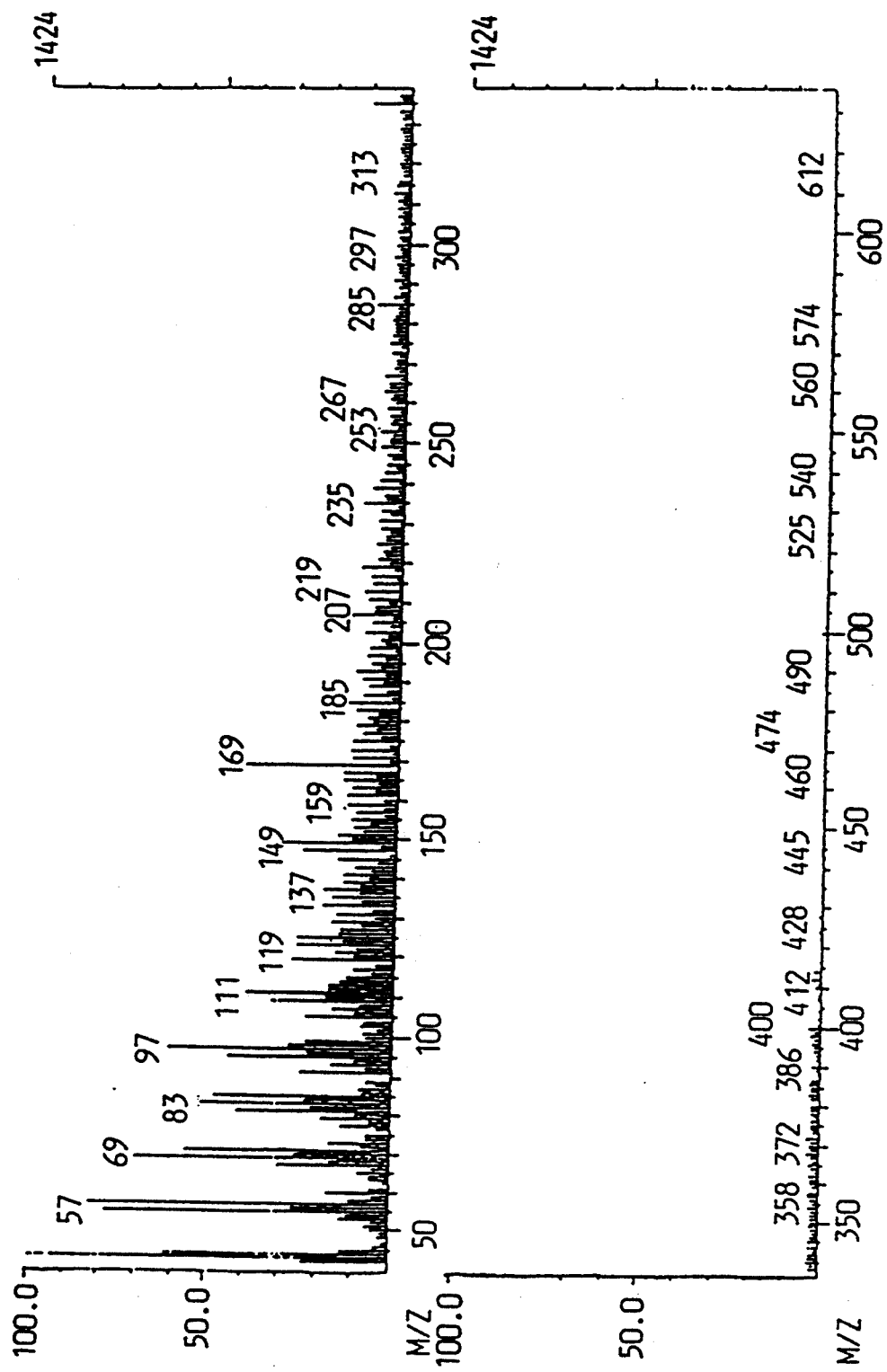
FIG. 1e shows the spectrum of region C of FIG. 1a. Chromatogram information for FIG. 1e is MASS SPECTRUM; Feb. 04, 1991 15:39:00+2:25; SAMPLE: PROV D (50%D); CONDS.: +/EI/Q1MASS SPECTRUM/GAIN:7/EM1200/IS150/EV70/SOLID; GC TEMP: 45 DEG. C; #140 TO #150 AVERAGED; DATA:XTRN020408 #145; BASE M/Z:43; CALI: CALI910204Q1 #2; RIC:45120.
Figure 1F:
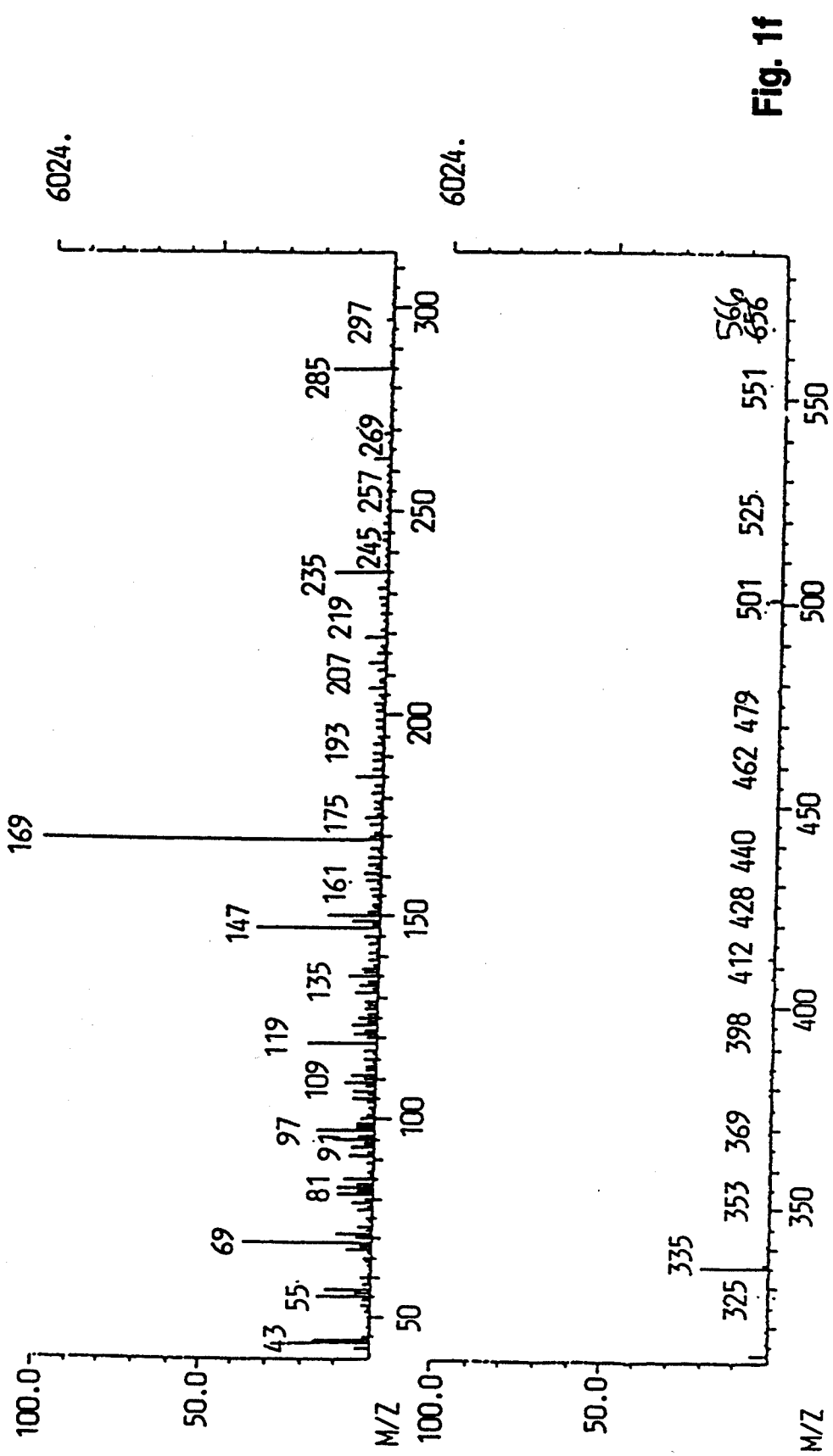
FIG. 1f shows the spectrum of region D of FIG. 1a. Chromatogram information for FIG. 1f is MASS SPECTRUM; Feb. 04, 1991 15:39:00+4:05; SAMPLE: PROV D (50%D); CONDS.: +/EI/Q1MASS SPECTRUM/GAIN:7/EM1200/IS150/EV70/SOLID; GC TEMP: 44 DEG. C; #240 TO #250 AVERAGED.
Figure 2C:
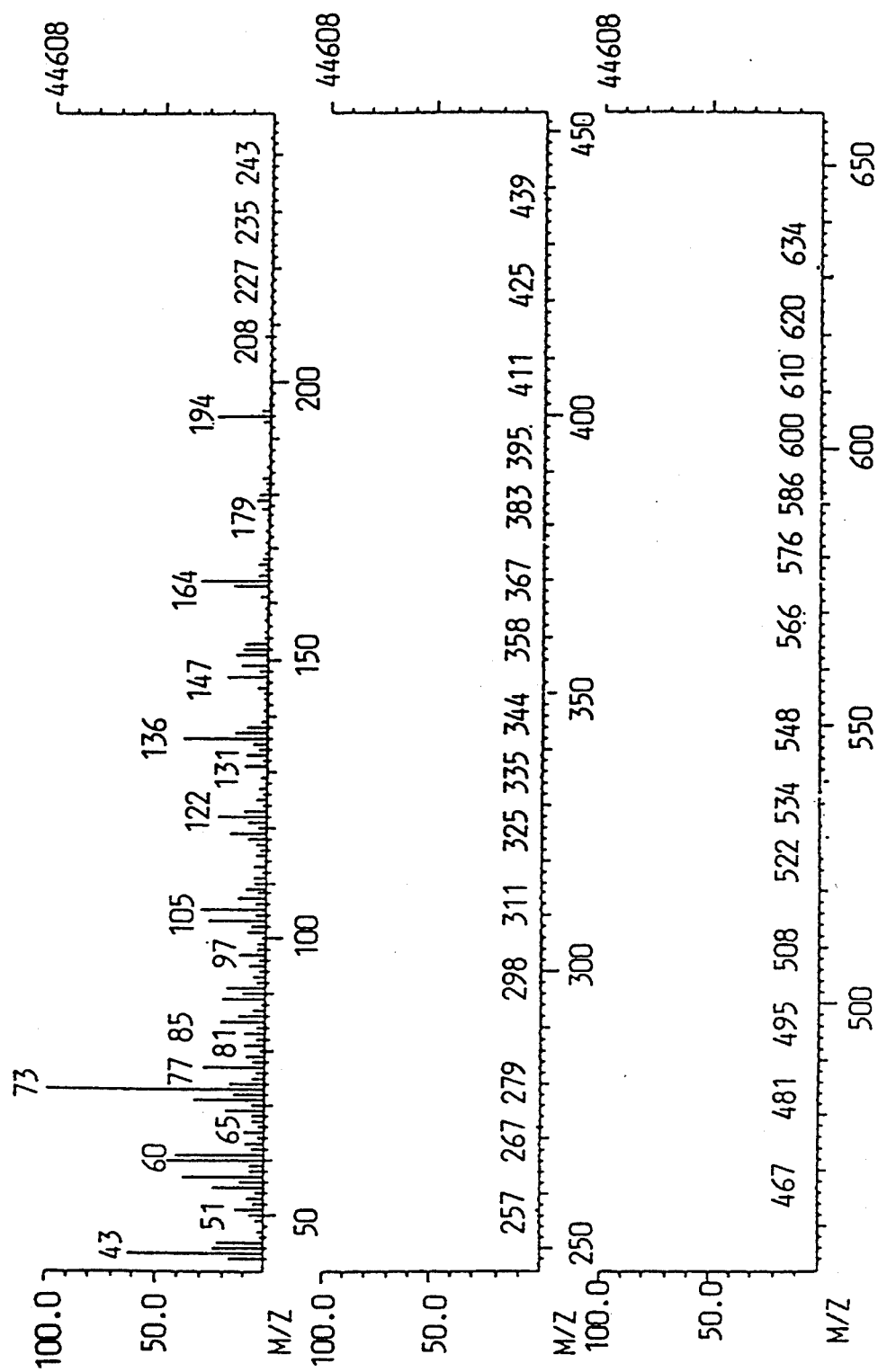

FIGS. 2a–2f show the corresponding spectra for the undialyzed product as are shown in FIGS. 1a–1f for the dialyzed product. Chromatogram information for FIGS. 2a and 2b is RIC; Feb. 04, 1991 15:39:00; SAMPLE: PROV C (50%); CONDS.: +/EI/Q1 MASS SPECTRUM/GAIN:7/EM1200/IS150/EV70-/SOLID; RANGE: G 1,295; LABEL: N O 4.0; BASE U 20, 3; DATA:XTRN020407 #1; XTRN020407$; CALI: CALI910204Q1 #2, CAL910204Q1 #4847; SCANS 1–290.

Chromatogram information for FIG. 2c is MASS SPECTRUM; Feb. 04, 1991 15:30:00+1:08; SAMPLE: PROV C (50%D); CONDS.: +/EI/Q1MASS SPECTRUM/GAIN:7/EM1200/IS150/EV70/SOLID; GC TEMP: 49 DEG. C; #65 TO #72 AVERAGED −#83 TO #94 −#55 TO #60 X1.00; DATA:XTRN020407 #68; BASE M/Z:73; CALI: CALI910204Q1 #2; RIC:623616.

Figure 2D:
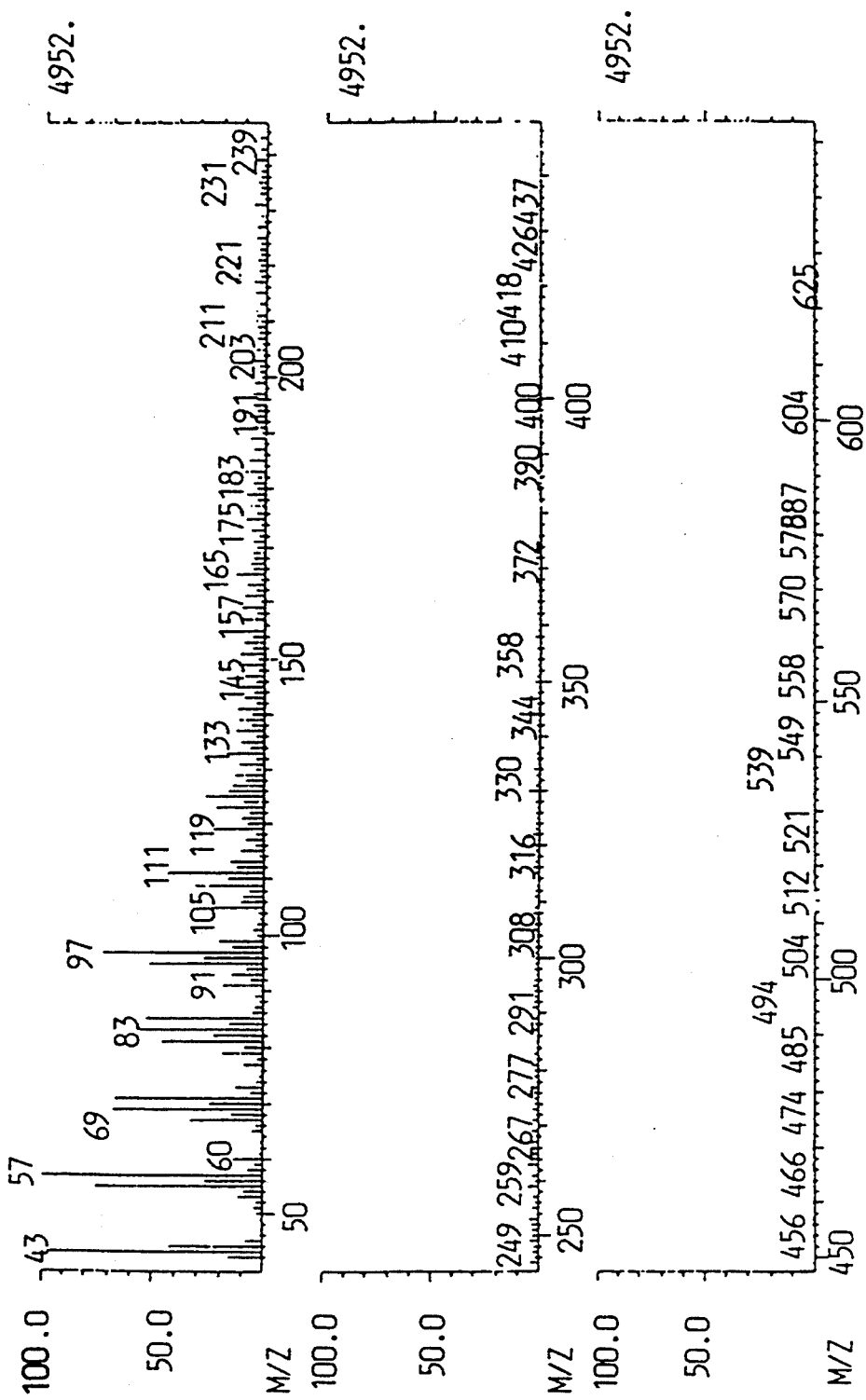

Chromatogram information for FIG. 2d is MASS SPECTRUM; Feb. 04, 1991 15:30:00+1:36; SAMPLE: PROV C (50%); CONDS.: +/EI/Q1MASS SPECTRUM/GAIN:7/EM1200/IS150/EV70/SOLID; GC TEMP: 48 DEG. C; #94 TO #99 AVERAGED −#109 TO #115 −#89 TO #93 X1.00; DATA:XTRN020407 #96; BASE M/Z:57; CALI: CALI910204Q1 #2; RIC:119424.

Figure 2E:
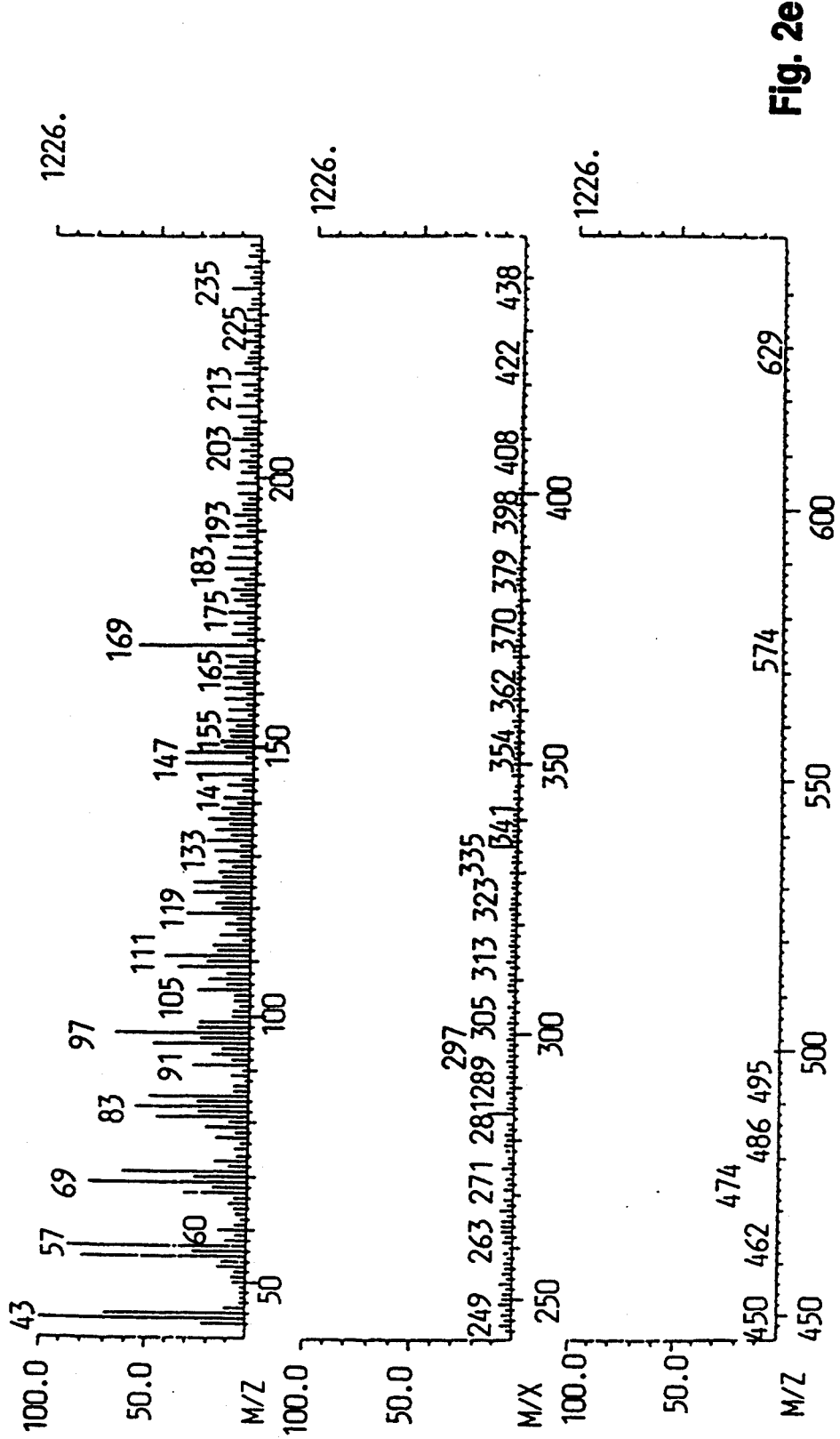

Chromatogram information for FIG. 2e is MASS SPECTRUM; Feb. 04, 1991 15:30:00+2:25; SAMPLE: PROV C (50%); CONDS.: +/EI/Q1MASS SPECTRUM/GAIN:7/EM1200/IS150/EV70/SOLID; GC TEMP: 48 DEG. C; #140 TO #150; DATA:XTRN020407 #145; BASE M/Z:43; CALI: CALI910204Q1 #2; RIC:42560.

Figure 2F:
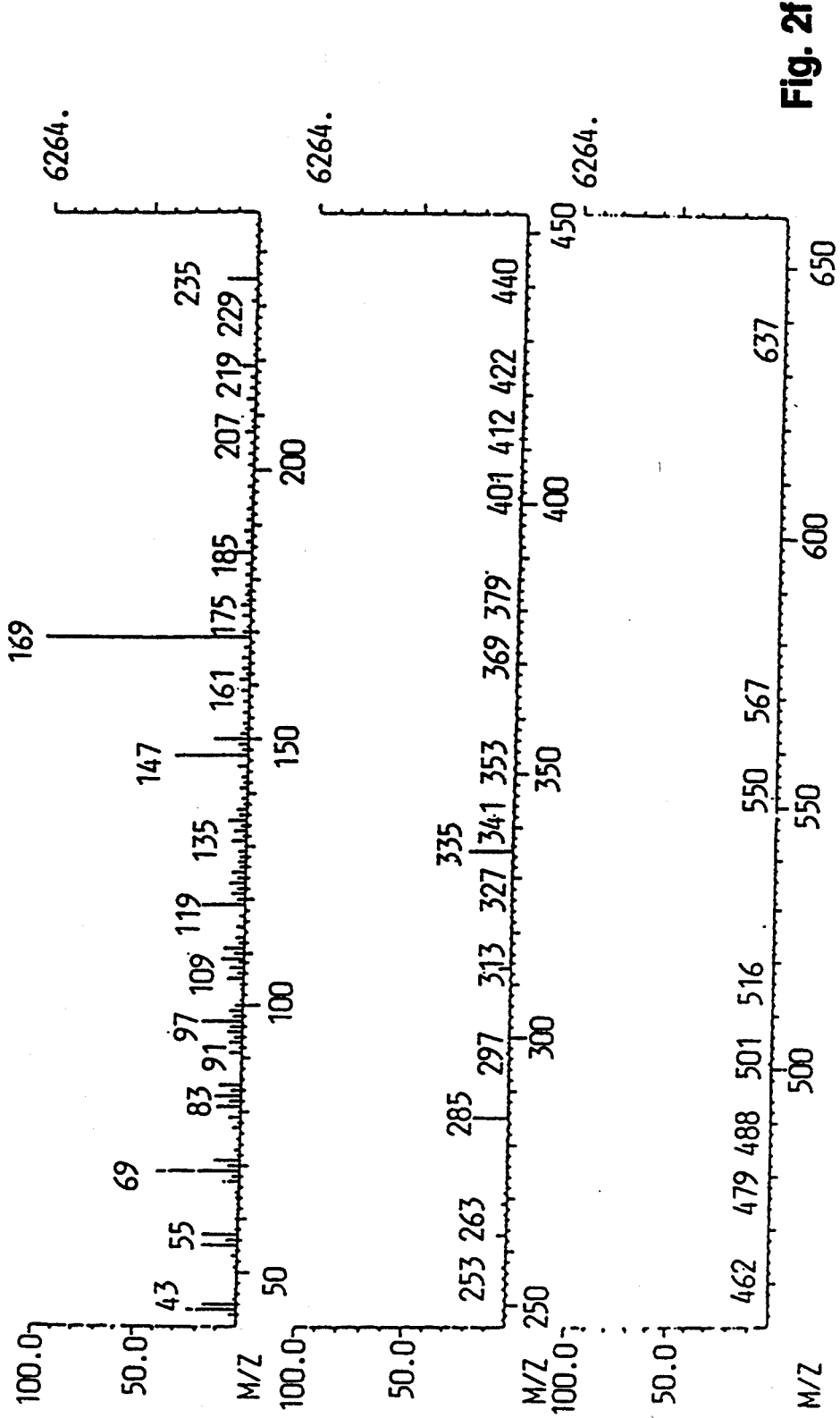

Chromatogram information for FIG. 2f is MASS SPECTRUM; Feb. 04, 1991, 15:30:00+4:05; SAMPLE: PROV C (50%); CONDS.: +/EI/Q1MASS SPECTRUM/GAIN:7/EM1200/IS150/EV70-/SOLID; GC TEMP: 47 DEG. C; #240 TO #250 AVERAGED; DATA:XTRN020407 #245; BASE M/Z:169; CALI: CALI910204Q1 #2; RIC:66560.

Figure 3:
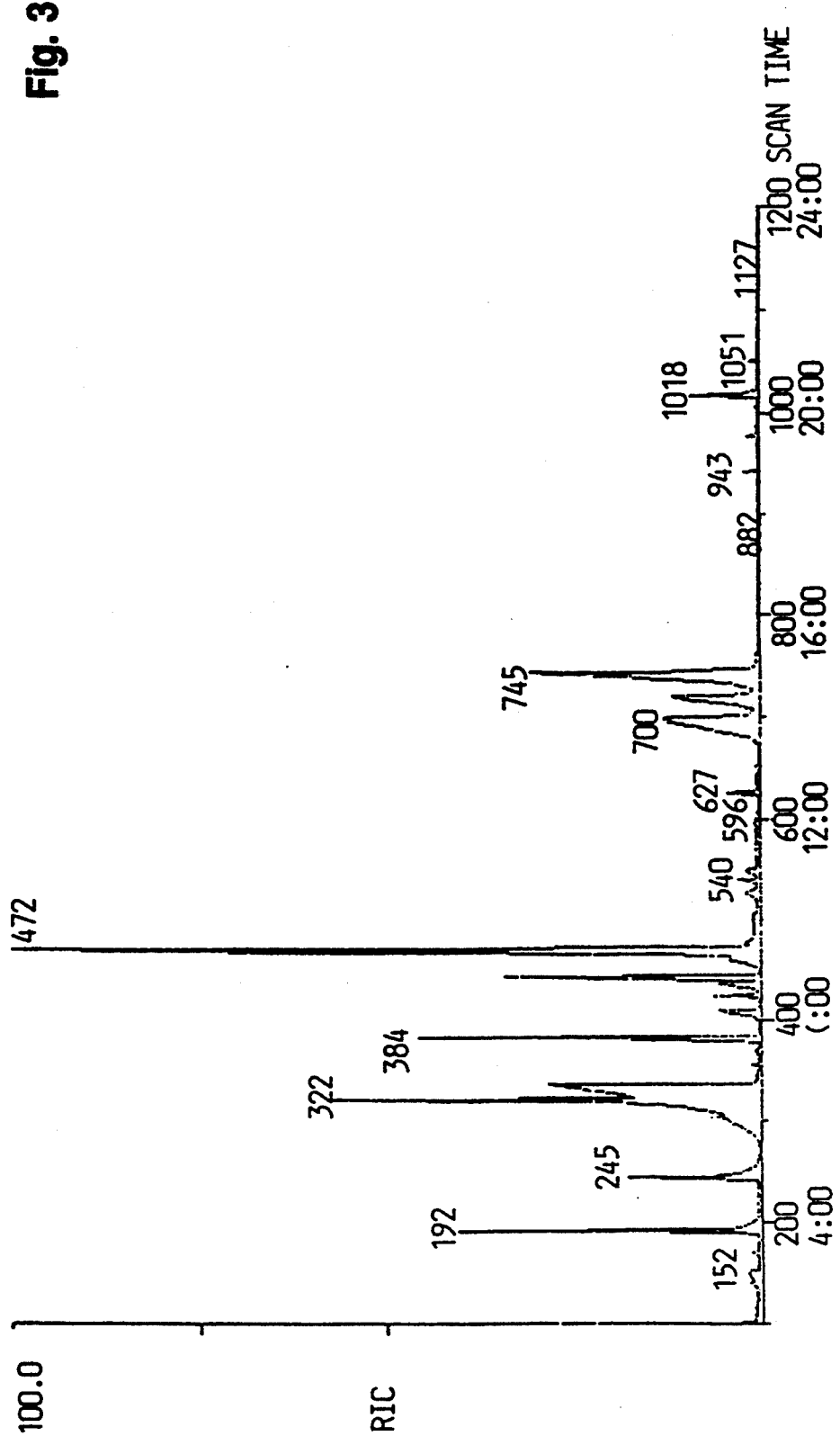

FIG. 3 shows the results of mass spectroscopy of Example 5 in particularly FIG. 3 shows the total ion chromatogram. Chromatogram information for FIG. 3 is RIC; Nov. 17, 1991 16:01:00; SAMPLE: PRP C; CONDS.: EI, TEMPPR; RANGE: G 1,379; LABEL: N O, 4.0; QUAN: A 0, 1.0 J O; BASE: U20, 3; DATA:MEX2 #192; SCANS 100–1200; CALI: SSCAL910917 #1.

Figure 4:
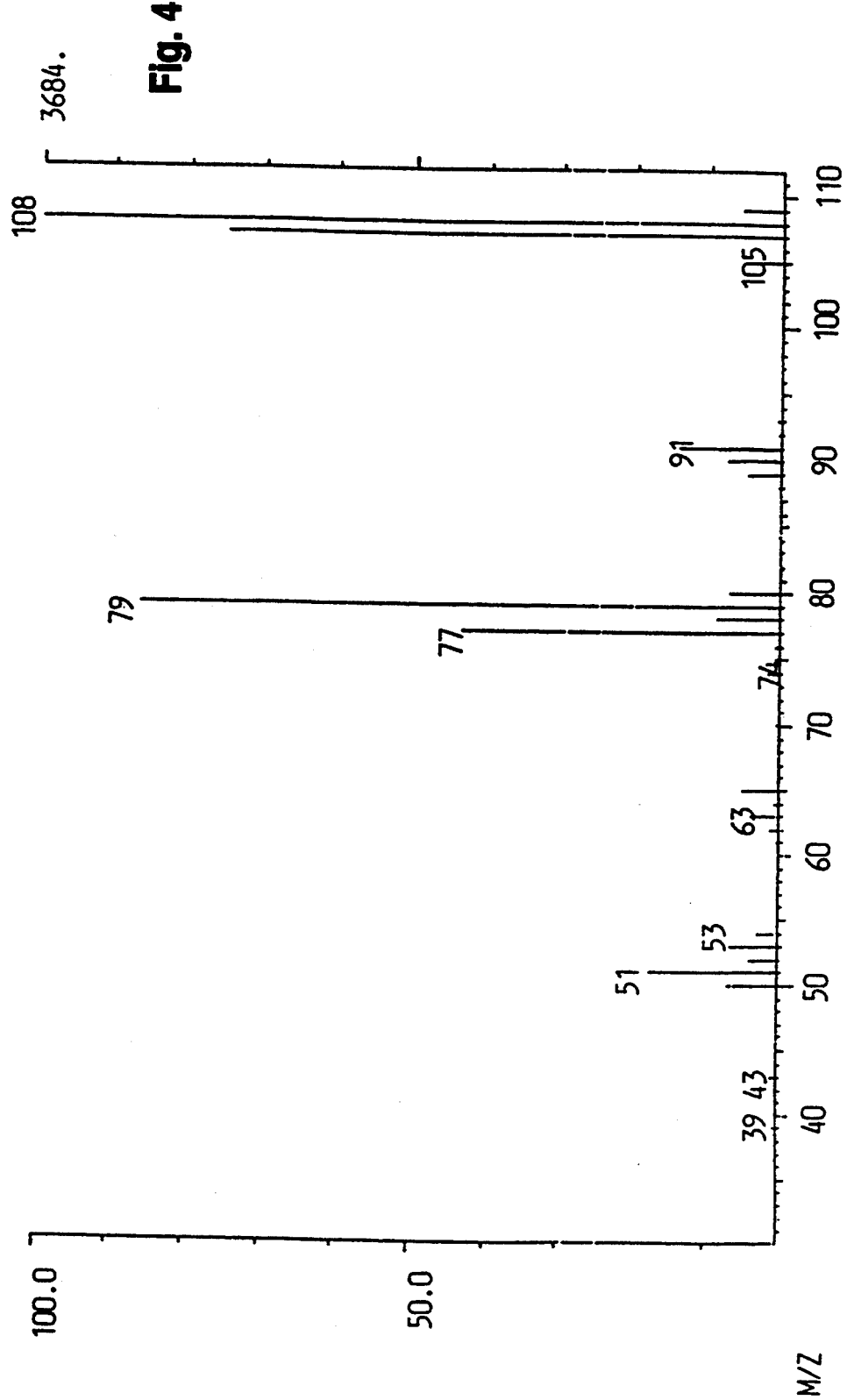

FIGS. 4–28 show the mass spectra for all peaks from the analysis of the chromatogram shown in FIG. 3. Chromatogram information for FIG. 4 is MASS SPECTRUM; Nov. 17, 1991 16:01:00+3:05; SAMPLE: PRP C; CONDS.: EI, TEMPPR; ENHANCED (S 15B 2N OT); DATA:MEX2 #192; BASE M/Z: 108; CALI: SSCAL910917 #1; RIC: 15024.

Figure 5:
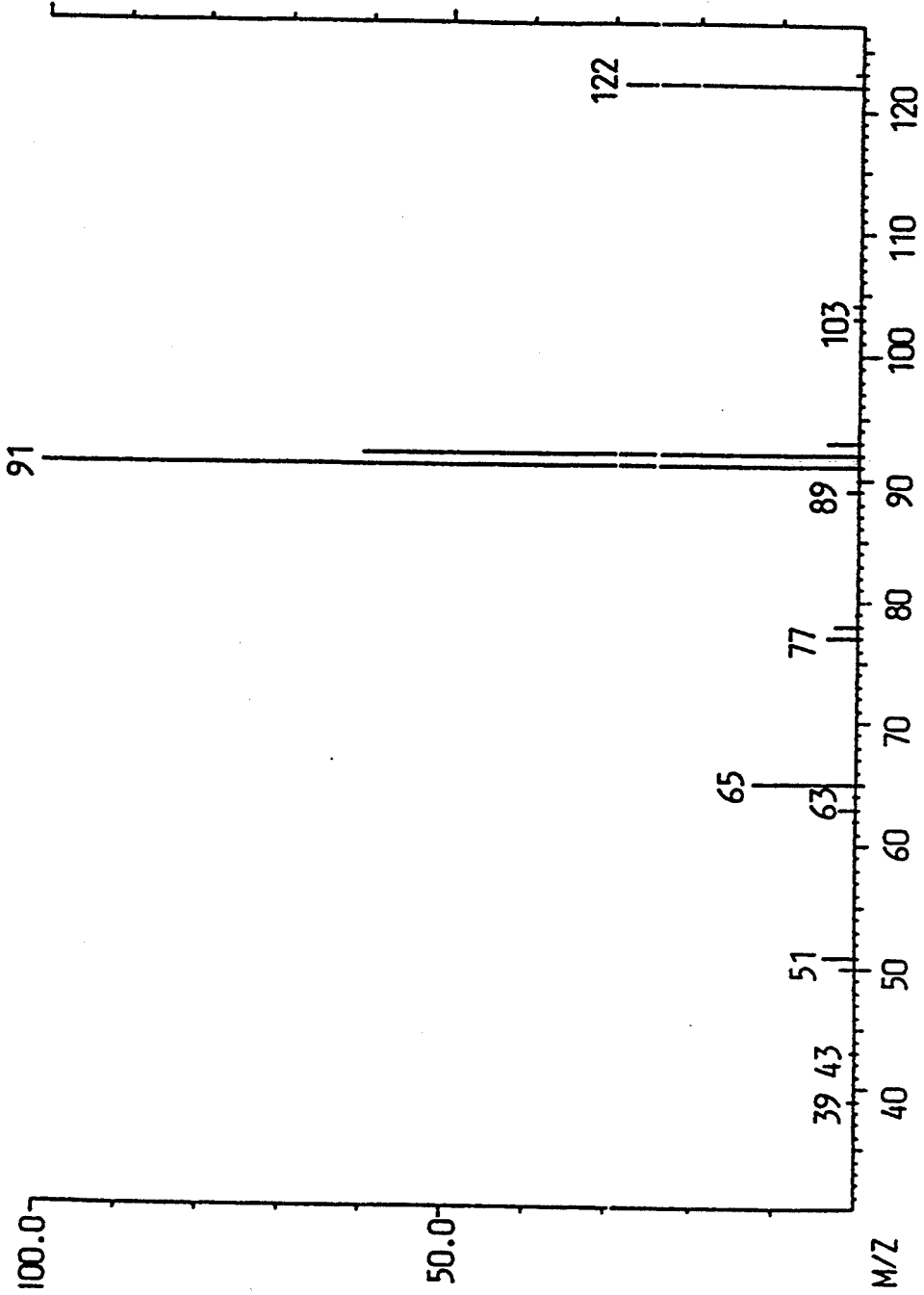

Chromatogram information for FIG. 5 is MASS SPECTRUM; Nov. 17, 1991 16:01:00+4:54; SAMPLE: PRP C; CONDS.: EI, TEMPPR; ENHANCED (S 15B 2N OT); DATA:MEX2 #245; BASE M/Z: 91; CALI: SSCAL910917 #1; RIC: 6752.

Figure 6:
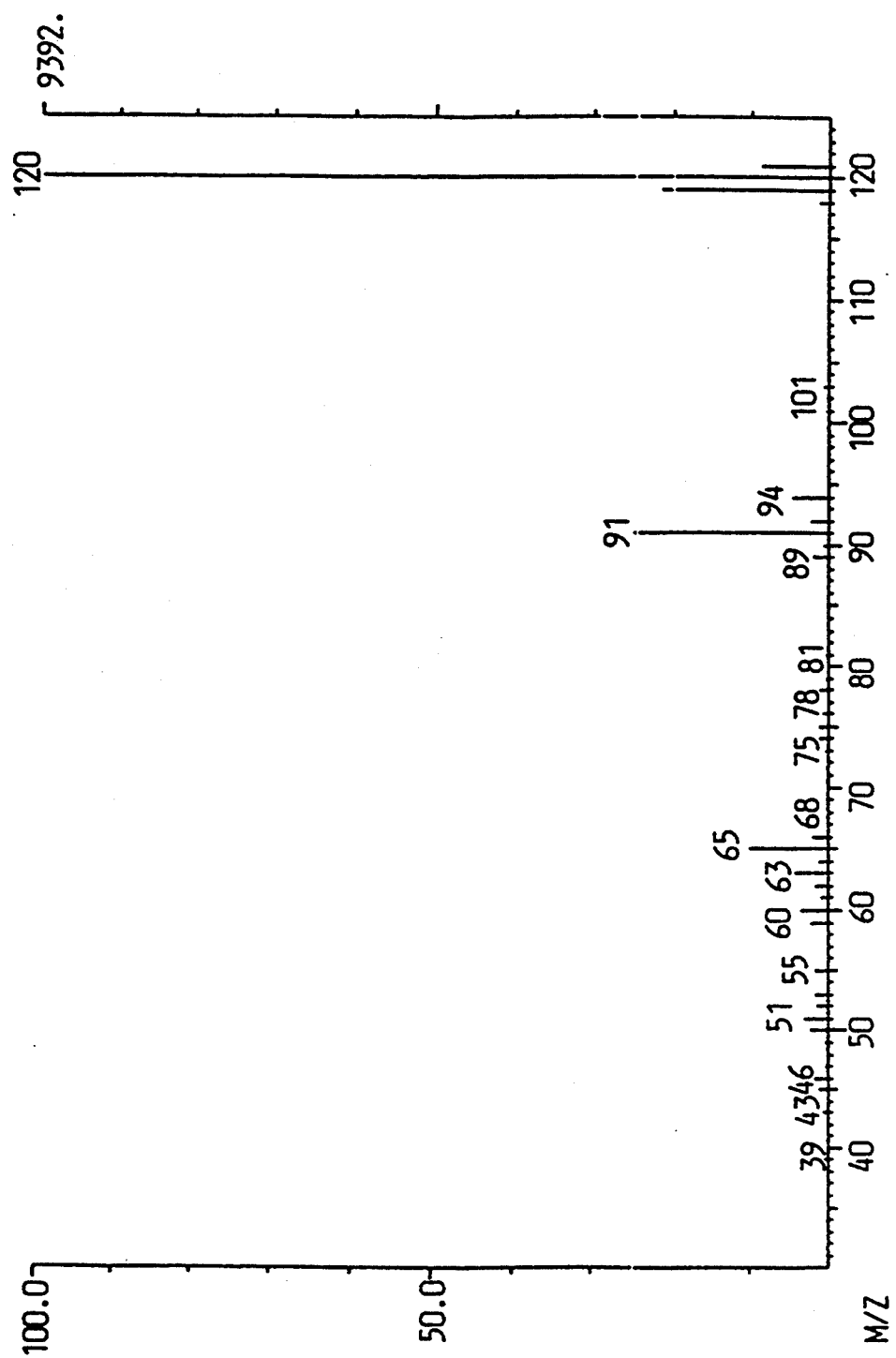

Chromatogram information for FIG. 6 is MASS SPECTRUM; Nov. 17, 1991 16:01:00+6:26; SAMPLE: PRP C; CONDS.: EI, TEMPPR; ENHANCED (S 15B 2N OT); DATA:MEX2 #322; BASE M/Z: 120; CALI: SSCAL910917 #1; RIC: 19712.

Figure 7:
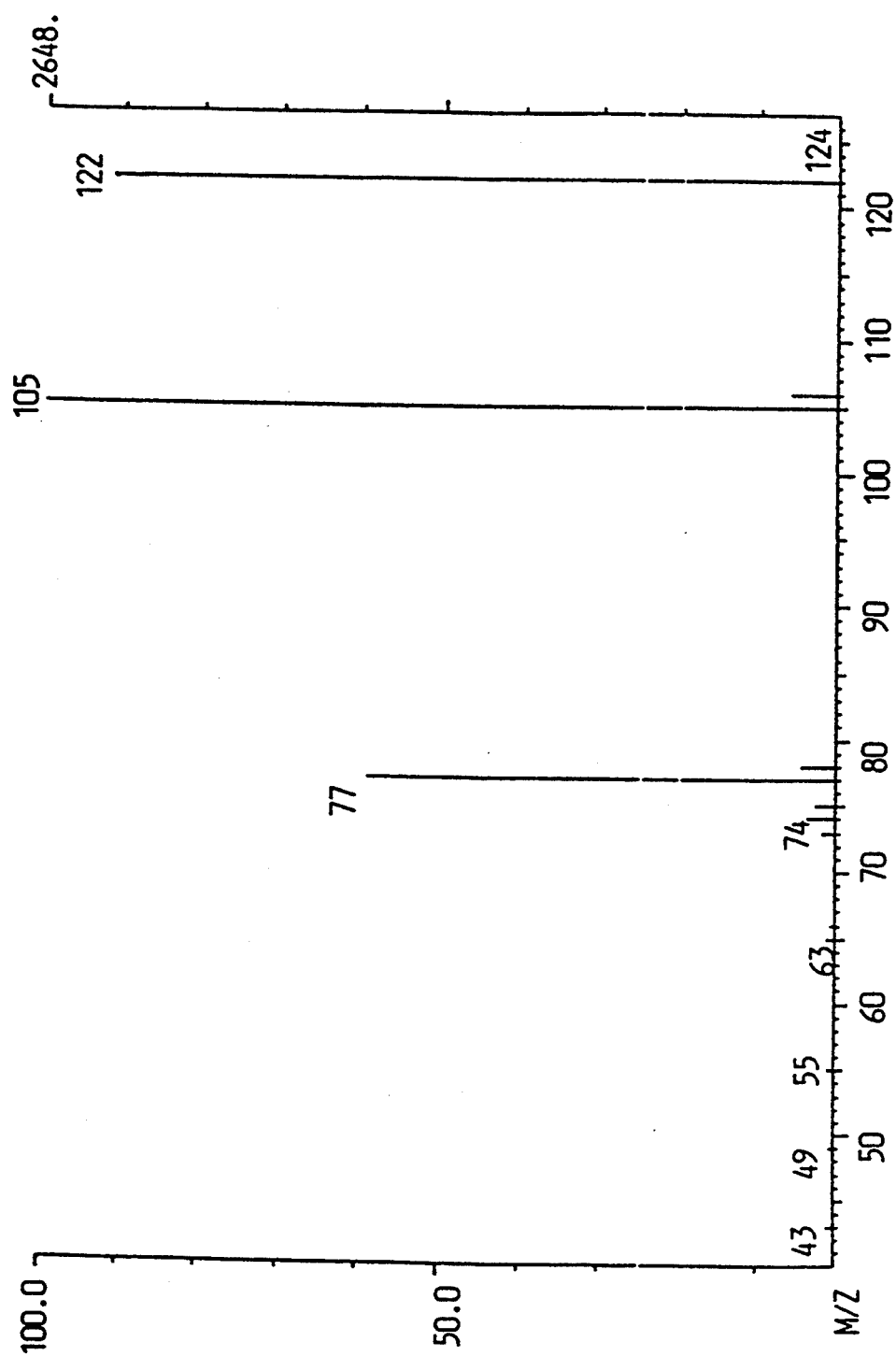

Chromatogram information for FIG. 7 is MASS SPECTRUM; Nov. 17, 1991 16:01:00+6:43; SAMPLE: PRP C; CONDS.: EI, TEMPPR; ENHANCED (S 15B 2N OT); DATA:MEX2 #336; BASE M/Z: 105; CALI: SSCAL910917 #1; RIC: 7200.

Figure 8:
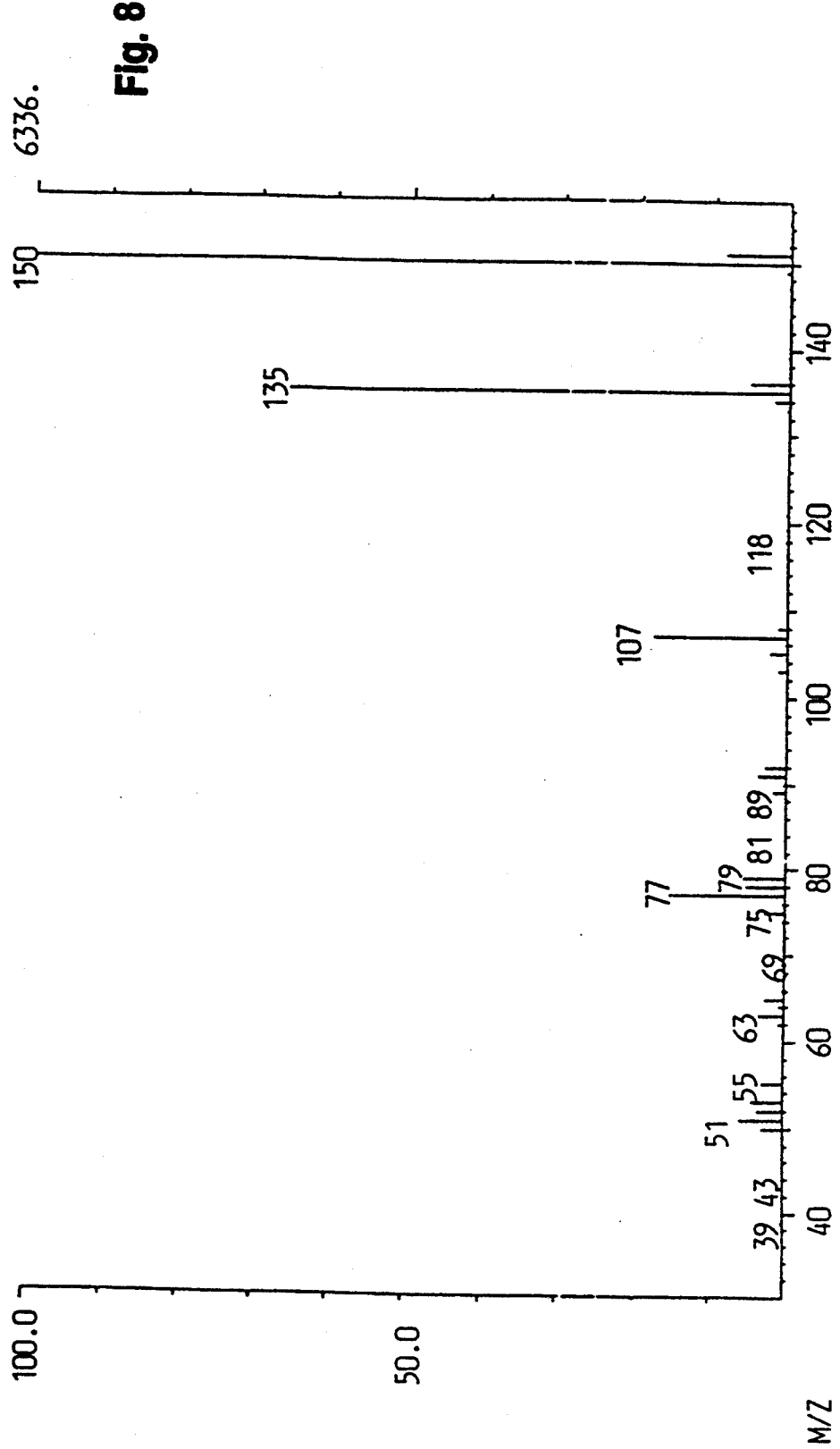

Chromatogram information for FIG. 8 is MASS SPECTRUM; Nov. 17, 1991 16:01:00+7:41; SAMPLE: PRP C; CONDS.: EI, TEMPPR; ENHANCED (S 15B 2N OT); DATA:MEX2 #384; BASE M/Z: 150; CALI: SSCAL910917 #1; RIC: 17184.

Figure 9:
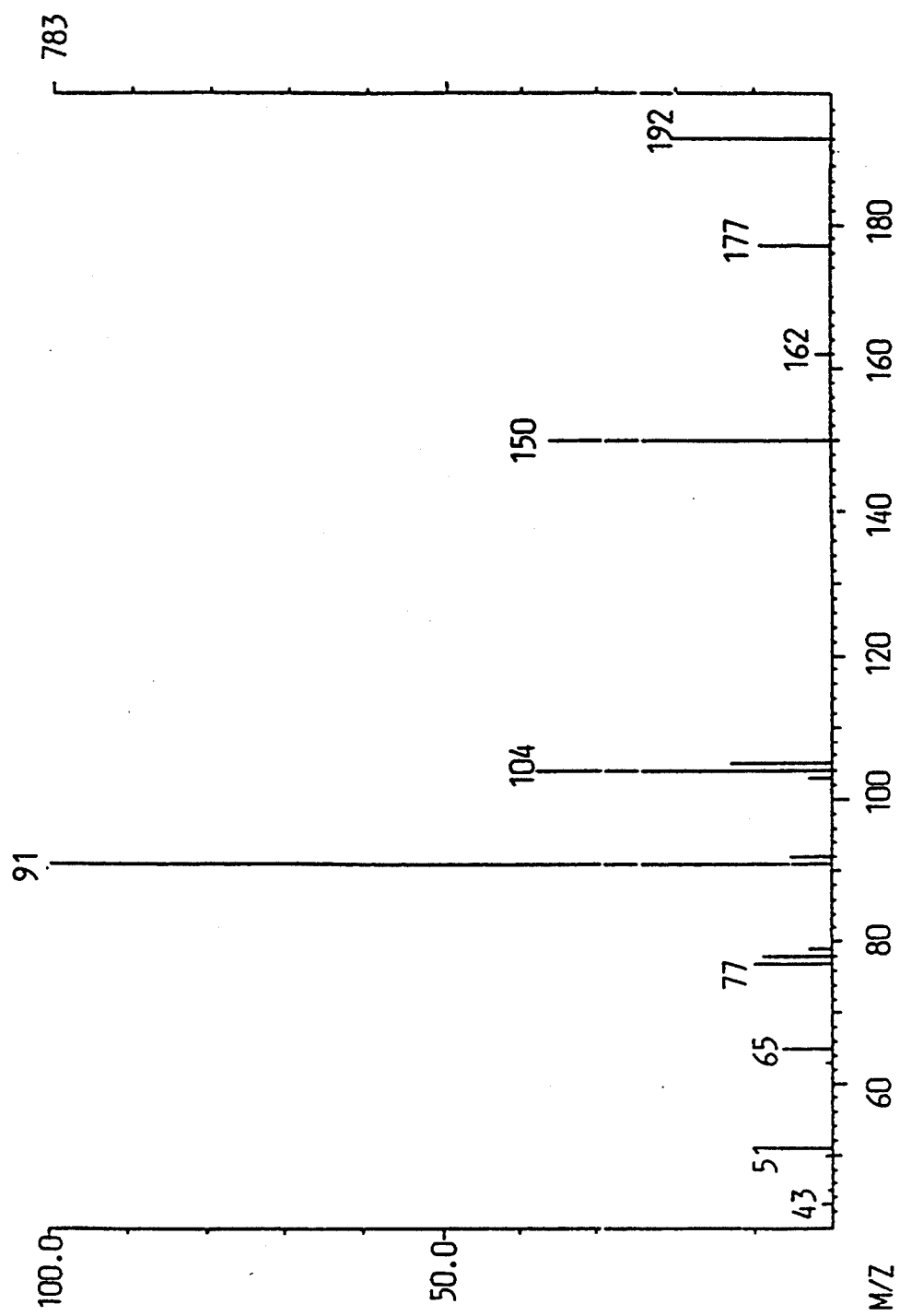

Chromatogram information for FIG. 9 is MASS SPECTRUM; Nov. 17, 1991 16:01:00+8:13; SAMPLE: PRP C; CONDS.: EI, TEMPPR; ENHANCED (S 15B 2N OT); DATA:MEX2 #411; BASE M/Z: 91; CALI: SSCAL910917 #1; RIC: 2088.

Figure 10:
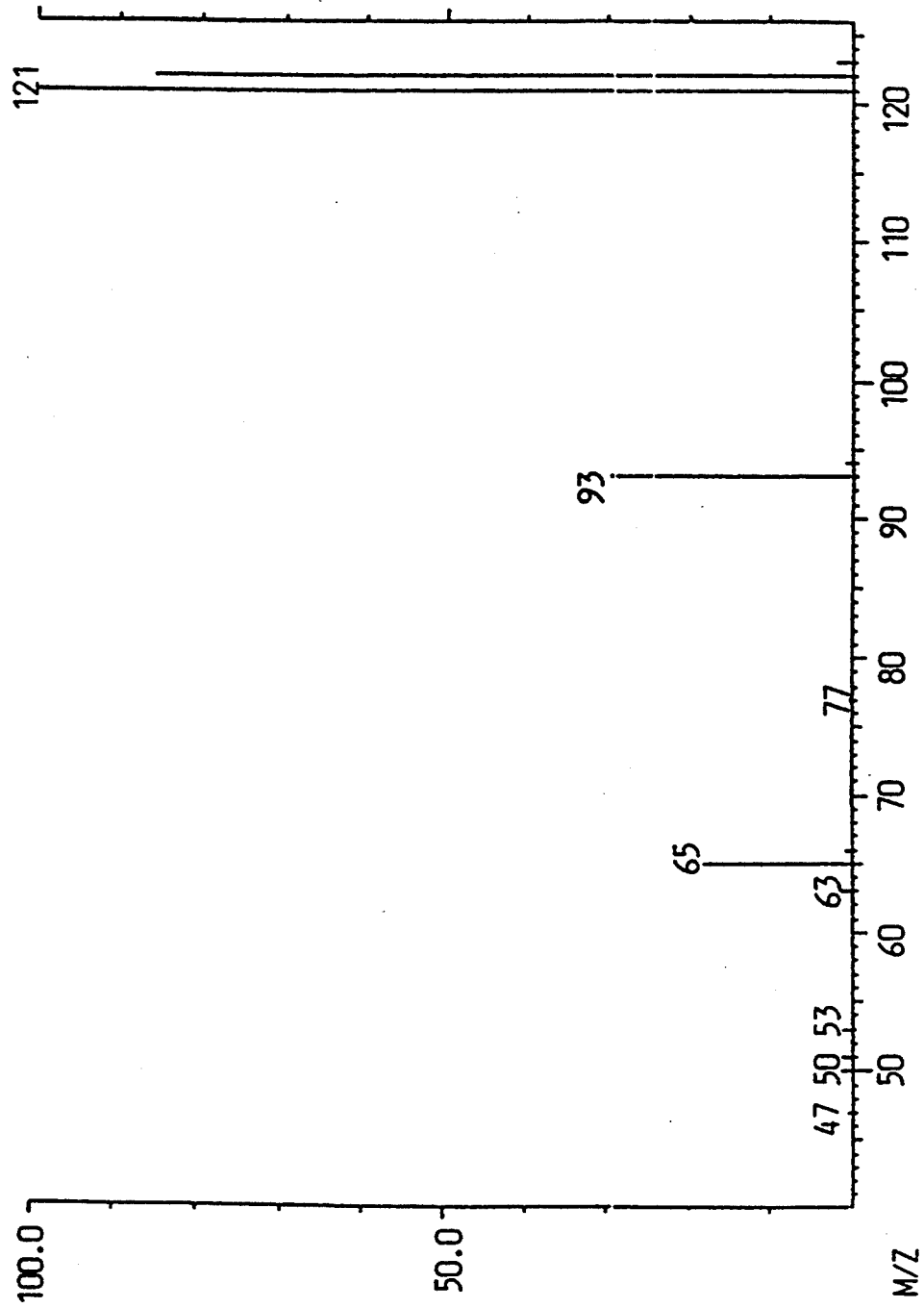

Chromatogram information for FIG. 10 is MASS SPECTRUM; Nov. 17, 1991 16:01:00+8:31; SAMPLE: PRP C; CONDS.: EI, TEMPPR; ENHANCED (S 15B 2N OT); DATA:MEX2 #426; BASE M/Z: 121; CALI: SSCAL910917 #1; RIC: 2256.

Figure 11:
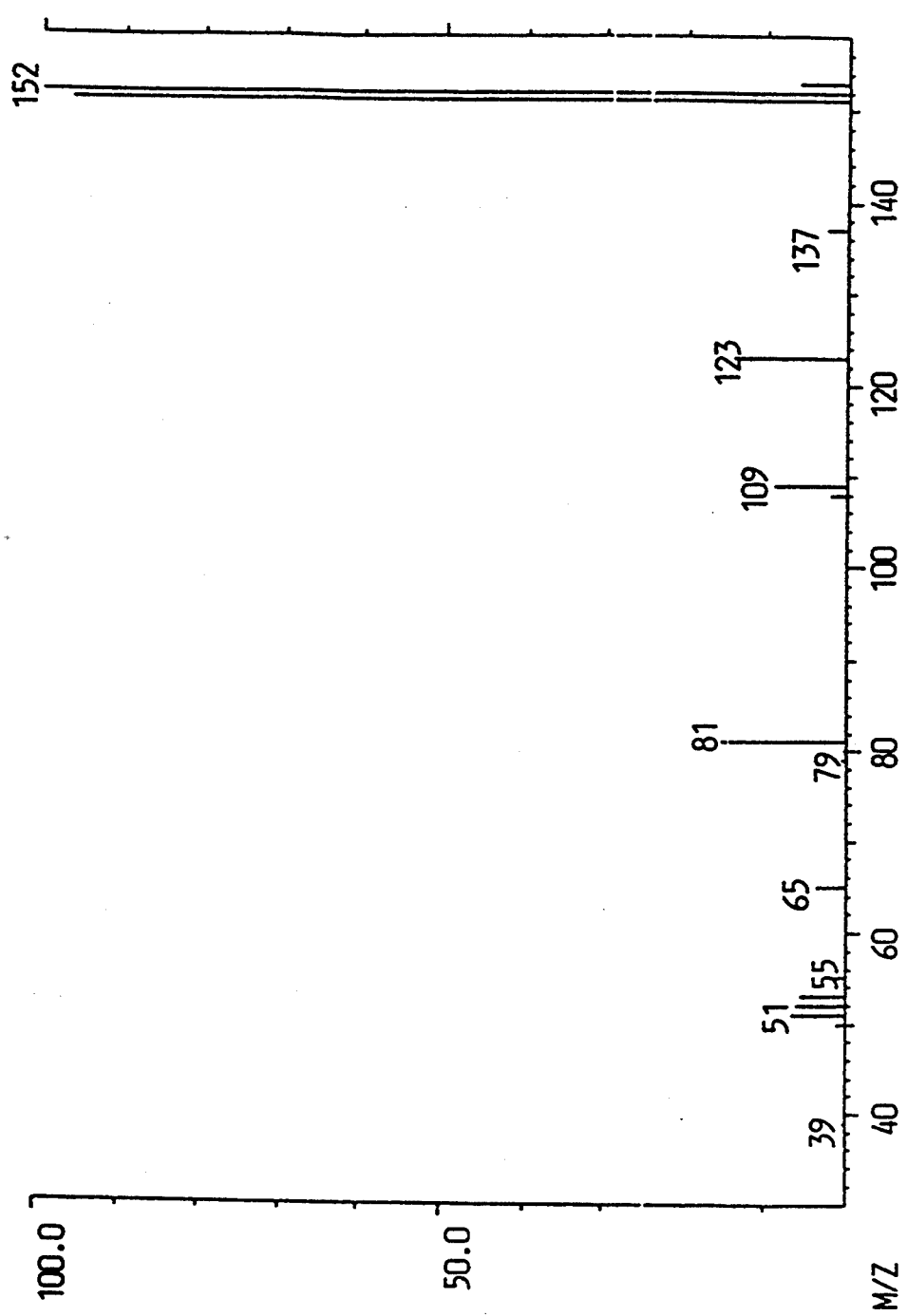

Chromatogram information for FIG. 11 is MASS SPECTRUM; Nov. 17, 1991 16:01:00+8:46; SAMPLE: PRP C; CONDS.: EI, TEMPPR; ENHANCED (S 15B 2N OT); DATA:MEX2 #438; BASE M/Z: 152; CALI: SSCAL910917 #1; RIC: 2380.

Figure 12:
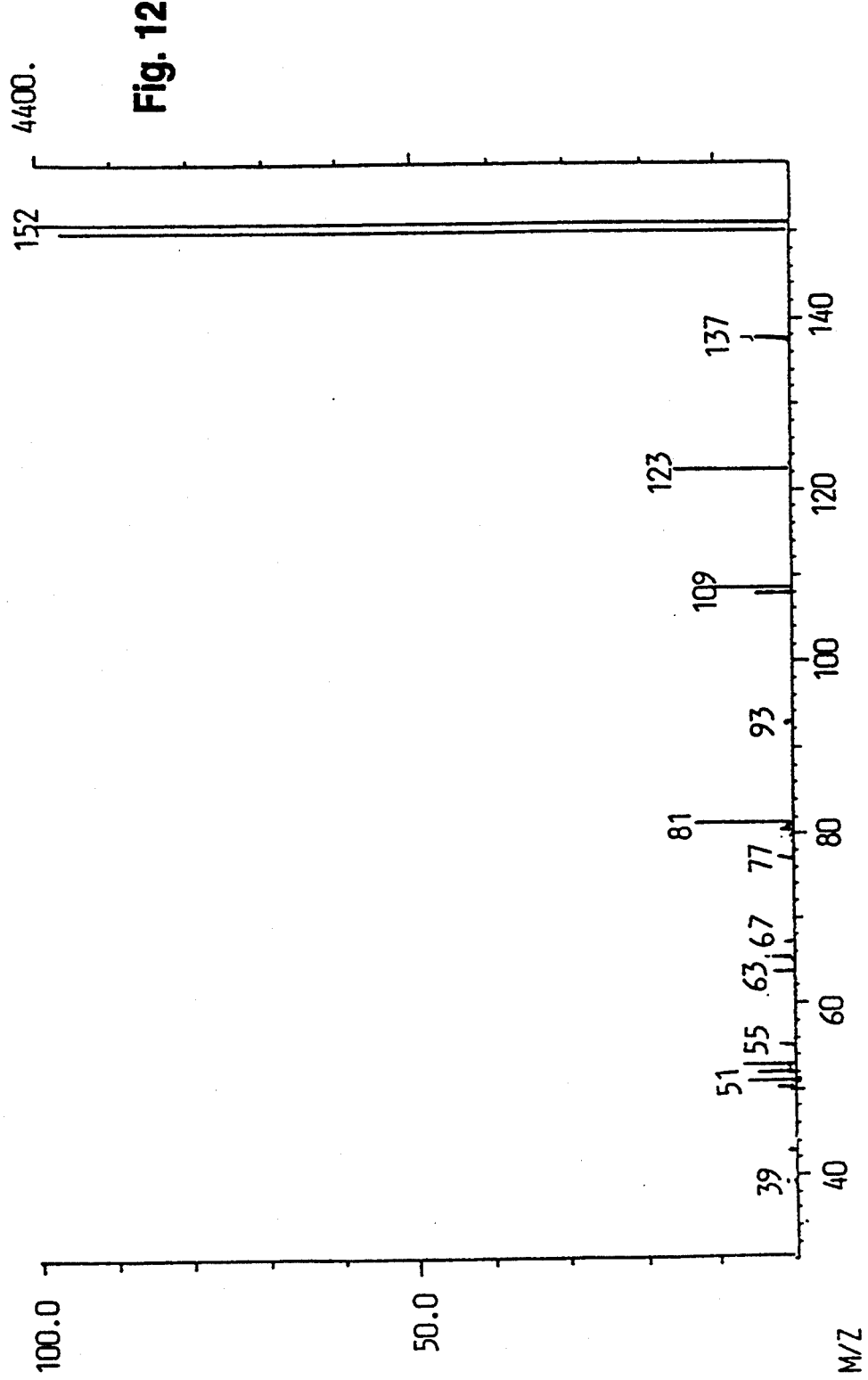

Chromatogram information for FIG. 12 is MASS SPECTRUM; Nov. 17, 1991 16:01:00+8:54; SAMPLE: PRP C; CONDS.: EI, TEMPPR; ENHANCED (S 15B 2N OT); DATA:MEX2 #445; BASE M/Z: 152; CALI: SSCAL910917 #1; RIC: 13712.

Figure 13:
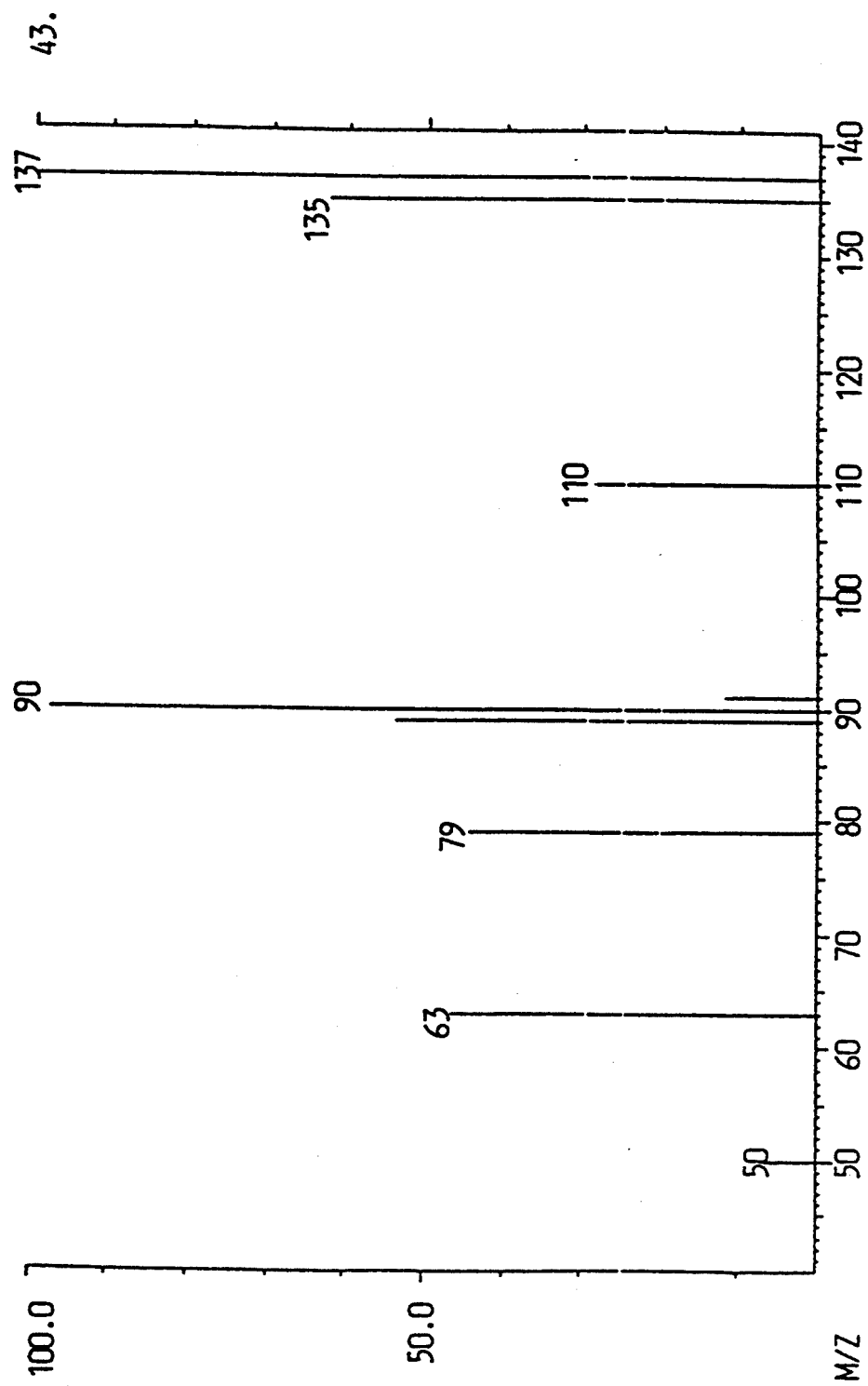

Chromatogram information for FIG. 13 is MASS SPECTRUM; Nov. 17, 1991 16:01:00+9:13; SAMPLE: PRP C; CONDS.: EI, TEMPPR; ENHANCED (S 15B 2N OT); DATA:MEX2 #461; BASE M/Z: 137; CALI: SSCAL910917 #1; RIC: 194.

Figure 14:
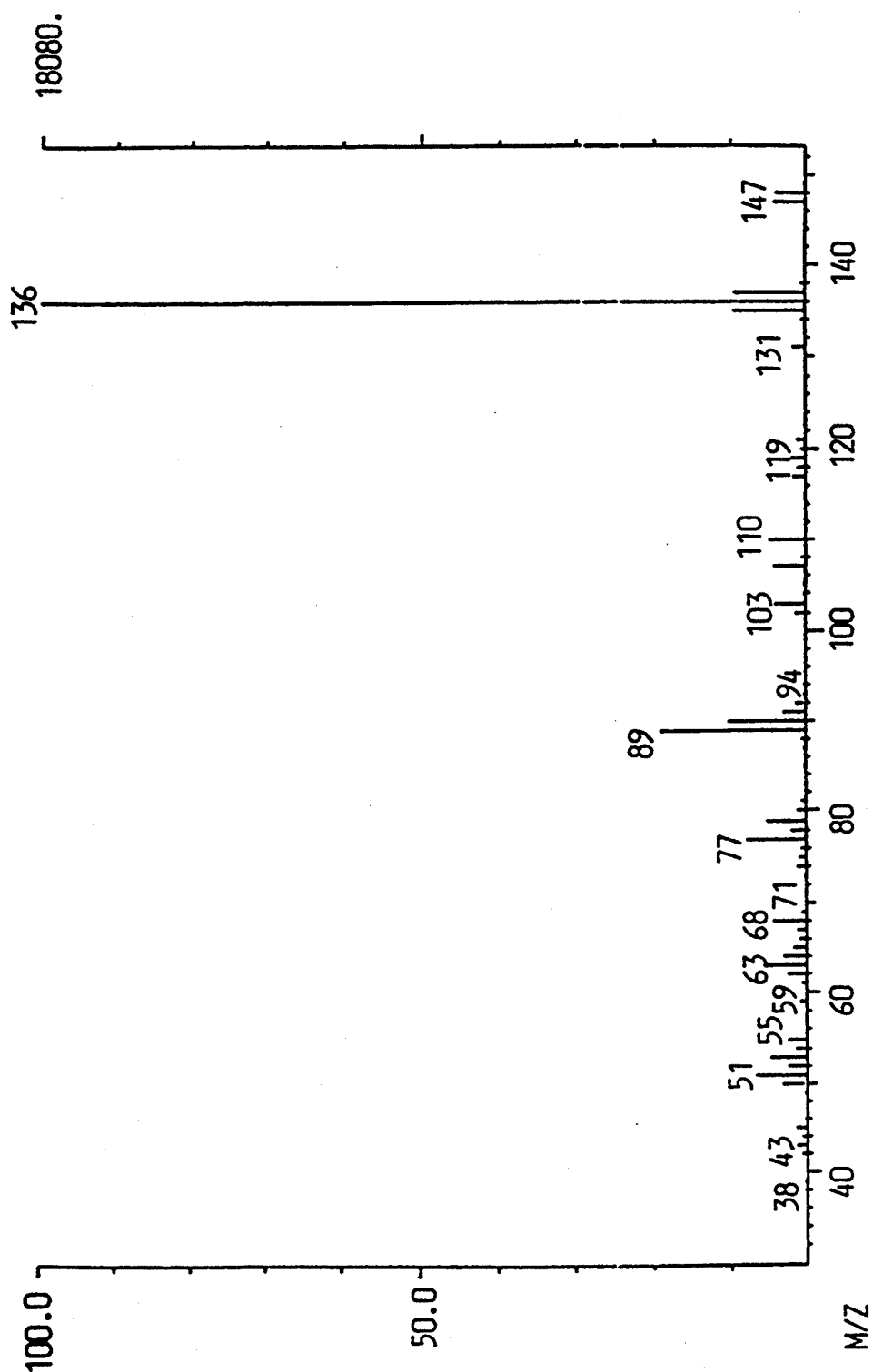

Chromatogram information for FIG. 14 is MASS SPECTRUM; Nov. 17, 1991 16:01:00+9:26; SAMPLE: PRP C; CONDS.: EI, TEMPPR; ENHANCED (S 15B 2N OT); DATA:MEX2 #472; BASE M/Z: 136; CALI: SSCAL910917 #1; RIC: 45952.

Figure 15:
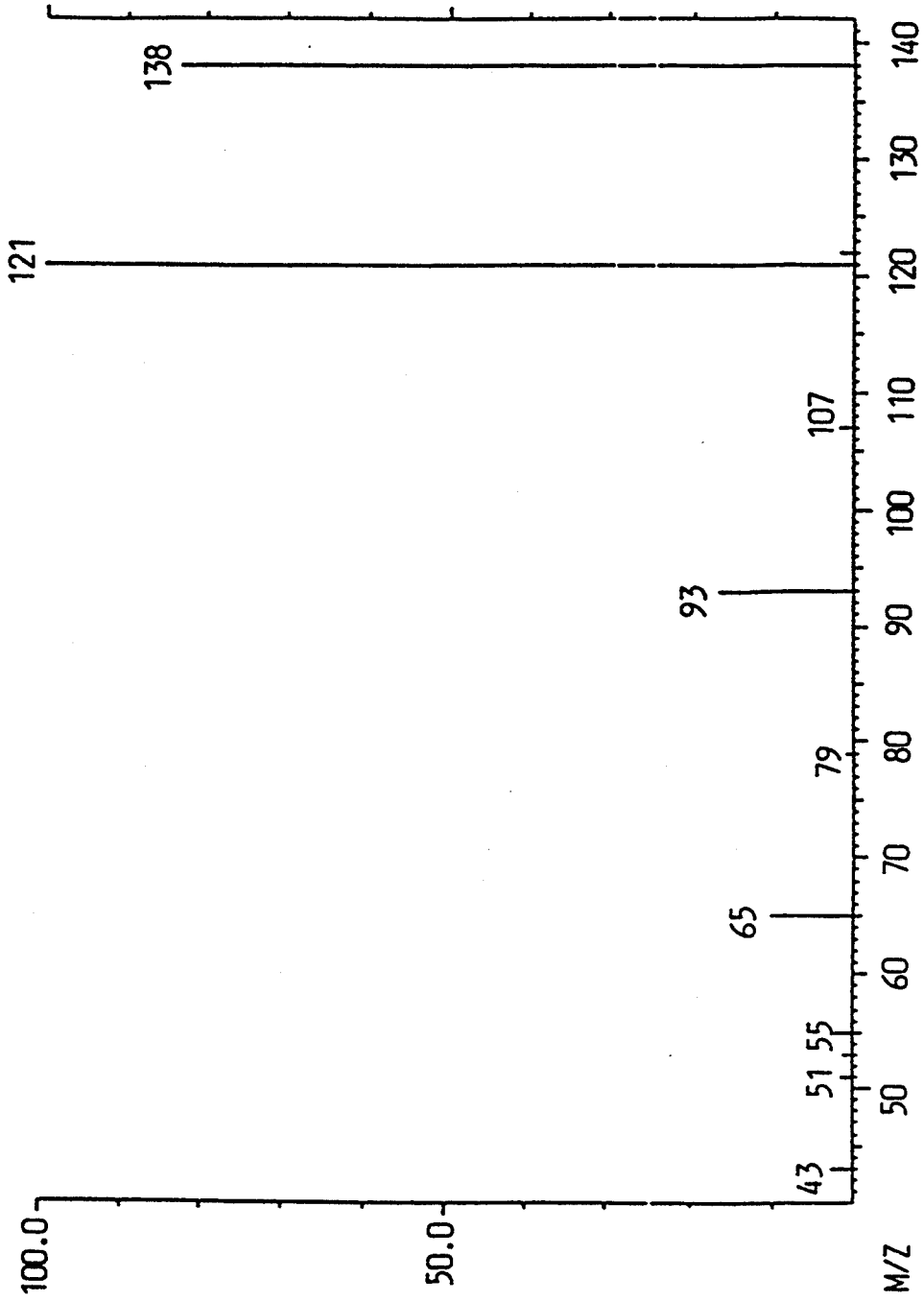

Chromatogram information for FIG. 15 is MASS SPECTRUM; Nov. 17, 1991 16:01:00+10:34; SAMPLE: PRP C; CONDS.: EI, TEMPPR; ENHANCED (S 15B 2N OT); DATA:MEX2 #528; BASE M/Z: 121; CALI: SSCAL910917 #1; RIC: 650.

Figure 16:
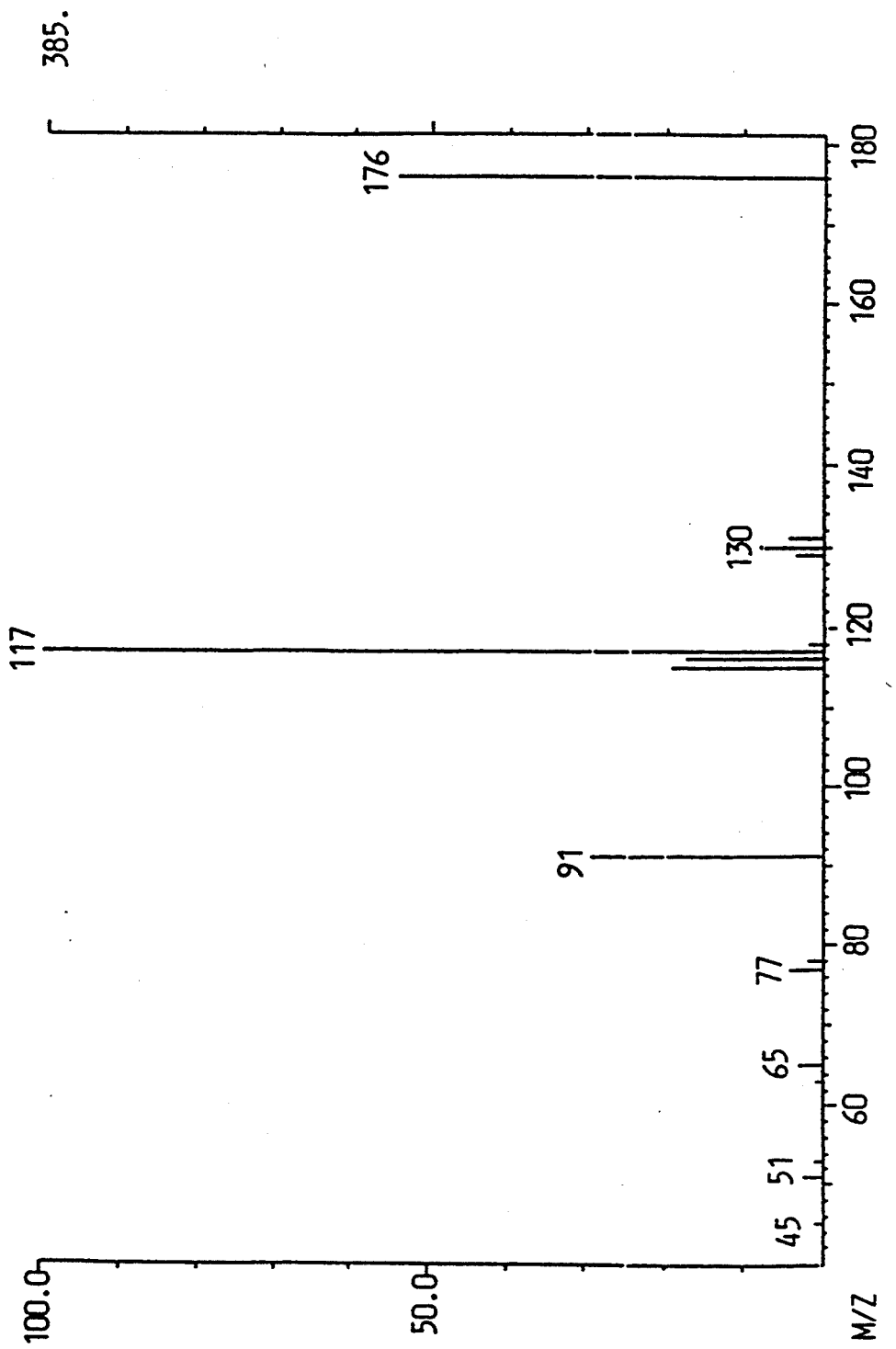

Chromatogram information for FIG. 16 is MASS SPECTRUM; Nov. 17, 1991 16:01:00+10:48; SAMPLE: PRP C; CONDS.: EI, TEMPPR; ENHANCED (S 15B 2N OT); DATA:MEX2 #540; BASE M/Z: 117; CALI: SSCAL910917 #1; RIC: 966.

Figure 17:
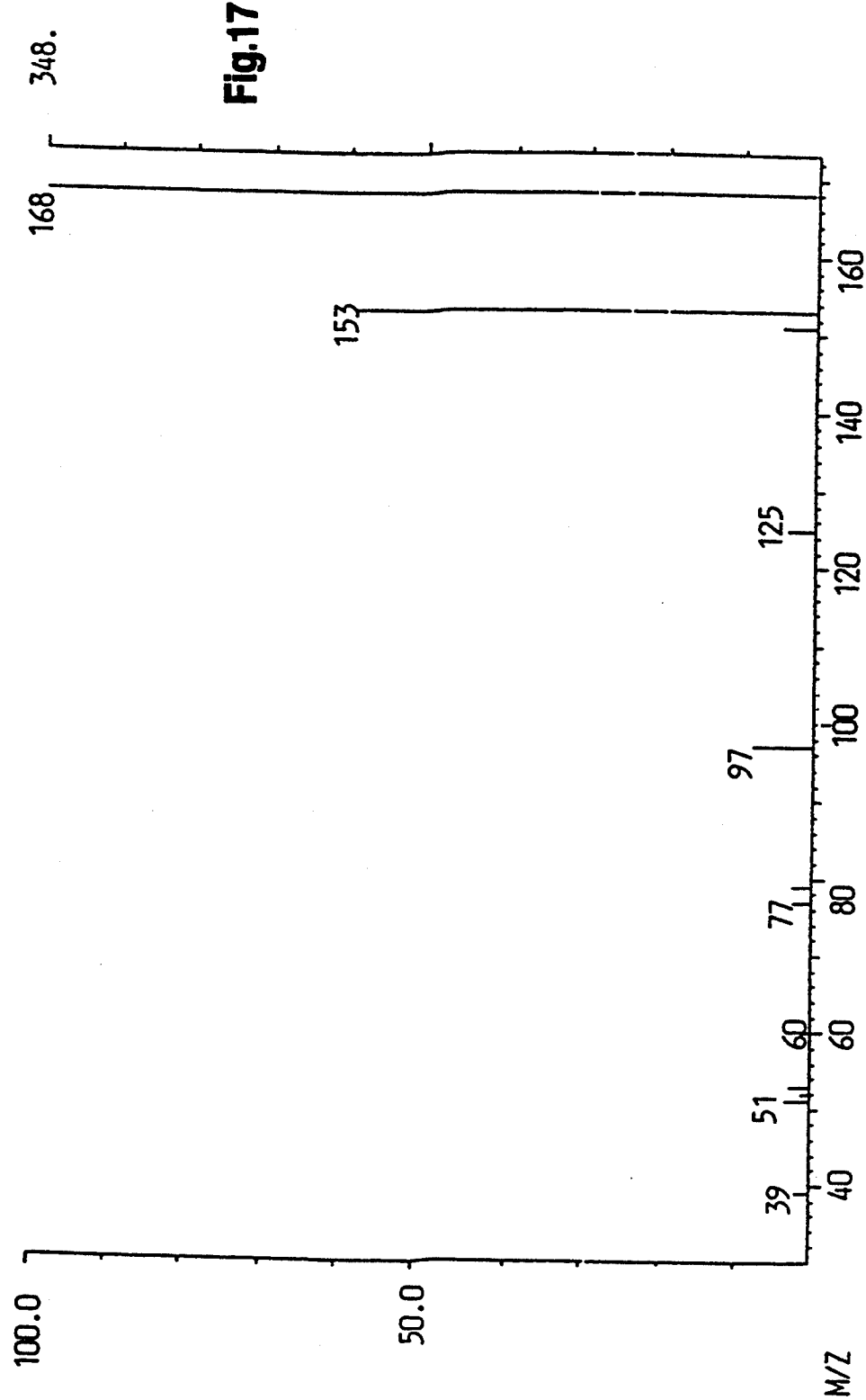

Chromatogram information for FIG. 17 is MASS SPECTRUM; Nov. 17, 1991 16:01:00+11:00; SAMPLE: PRP C; CONDS.: EI, TEMPPR; ENHANCED (S 15B 2N OT); DATA:MEX2 #550; BASE M/Z: 168; CALI: SSCAL910917 #1; RIC: 661.

Figure 18:
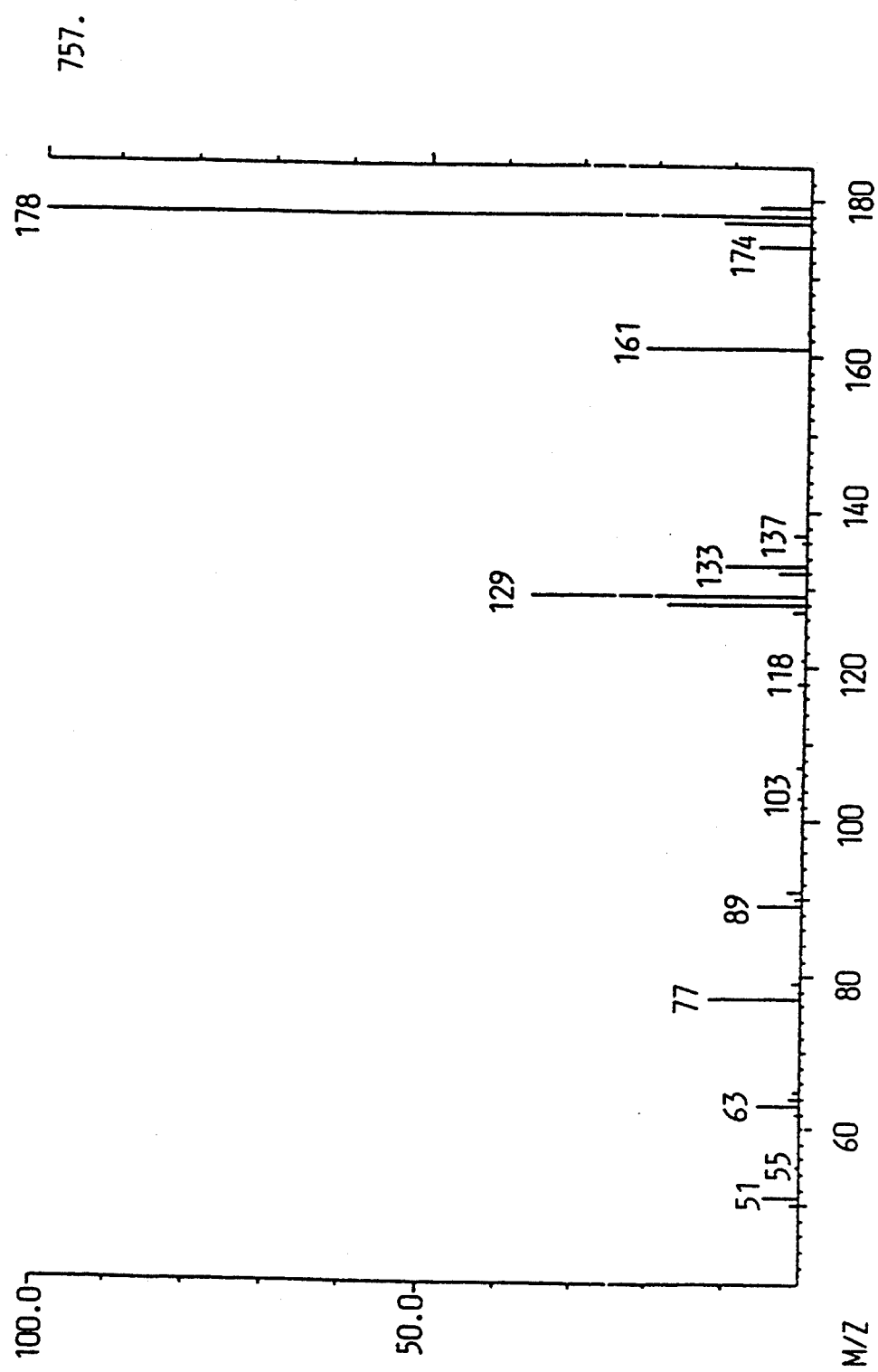

Chromatogram information for FIG. 18 is MASS SPECTRUM; Nov. 17, 1991 16:01:00+12:32; SAMPLE: PRP C; CONDS.: EI, TEMPPR; ENHANCED (S 15B 2N OT); DATA:MEX2 #627; BASE M/Z: 178; CALI: SSCAL910917 #1; RIC: 1952.

Figure 19:
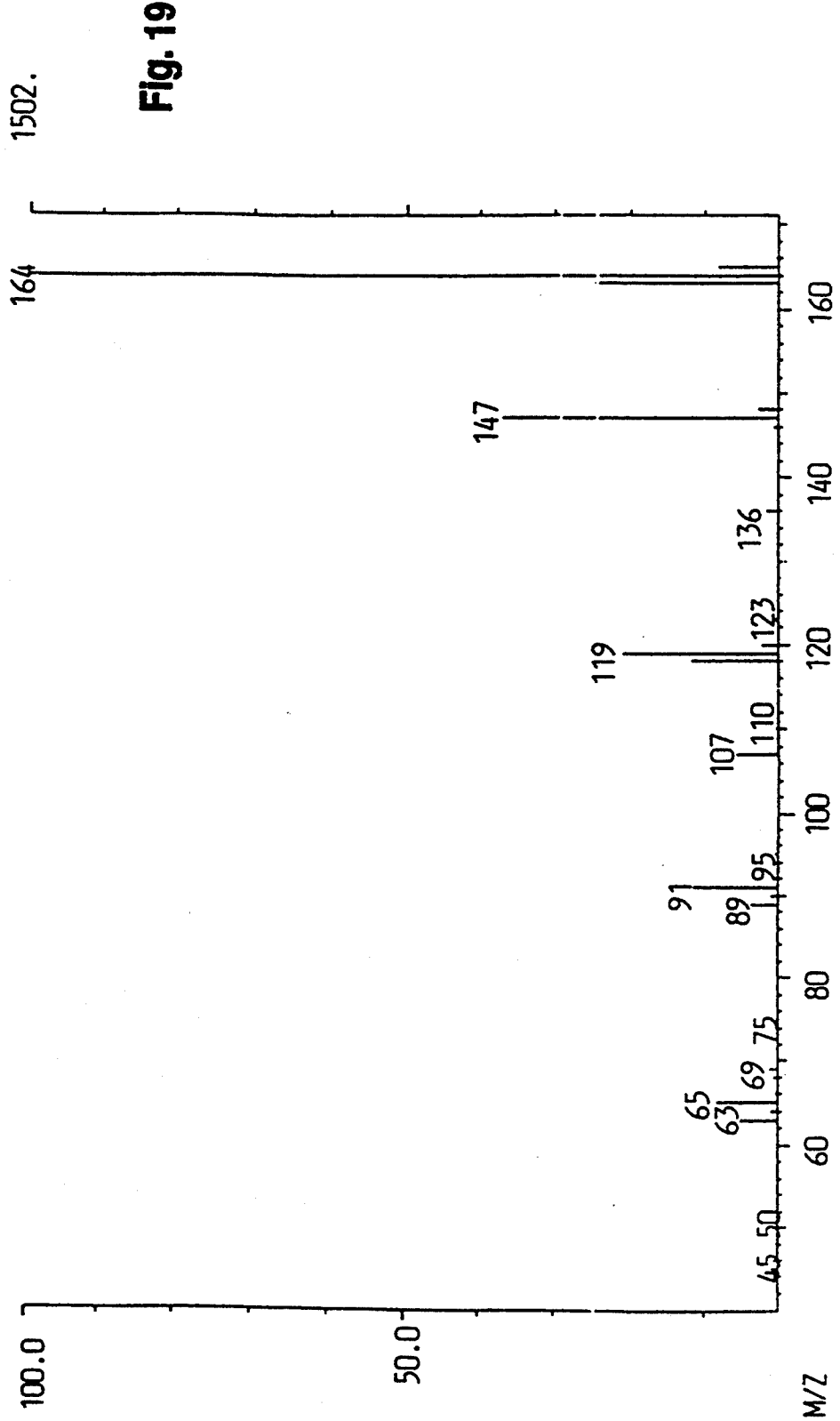

Chromatogram information for FIG. 19 is MASS SPECTRUM; Nov. 17, 1991 16:01:00+14:00; SAMPLE: PRP C; CONDS.: EI, TEMPPR; ENHANCED (S 15B 2N OT); DATA:MEX2 #700; BASE M/Z: 164; CALI: SSCAL910917 #1; RIC: 3784.

Figure 20:
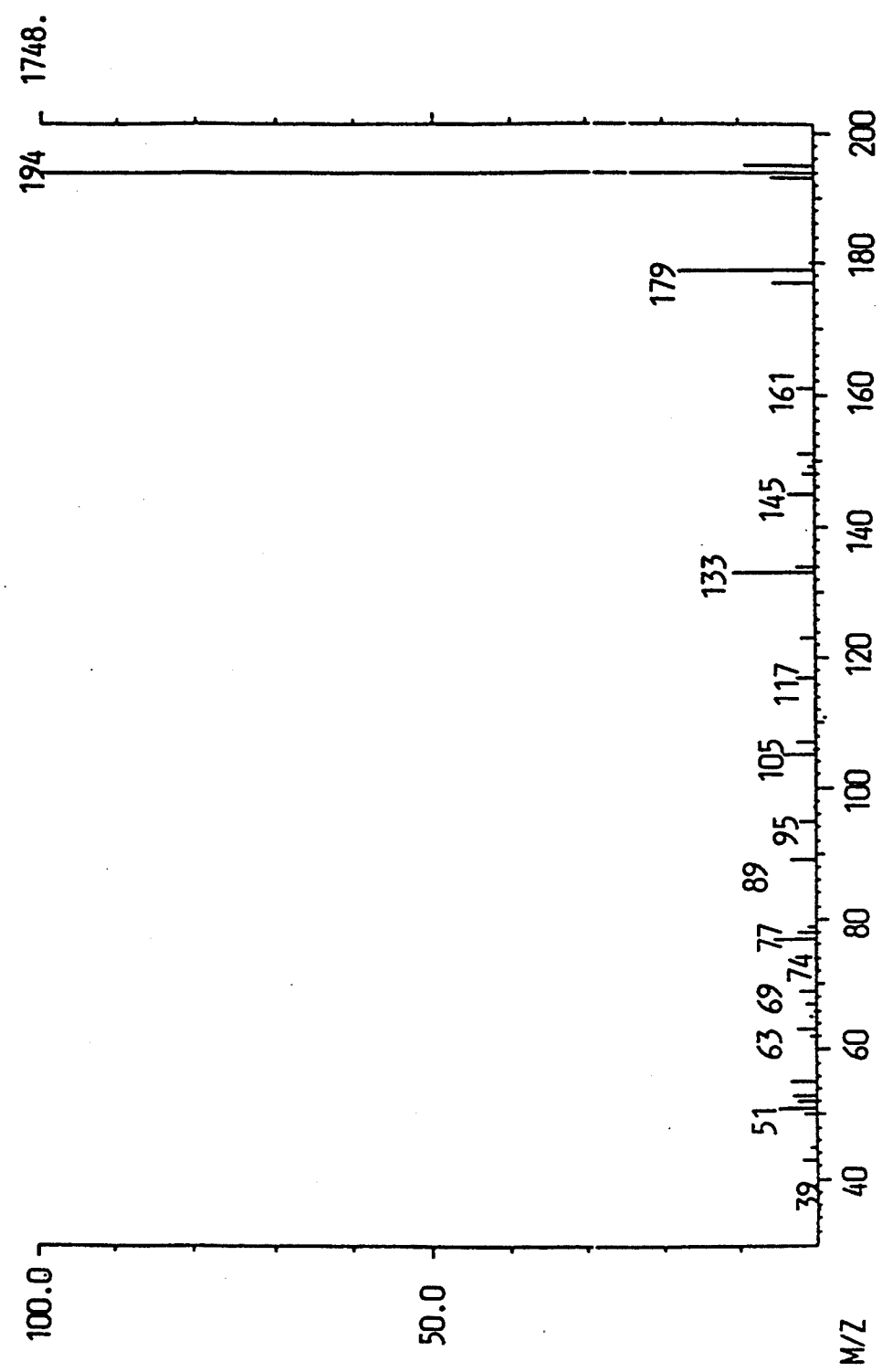

Chromatogram information for FIG. 20 is MASS SPECTRUM; Nov. 17, 1991 16:01:00+14:26; SAMPLE: PRP C; CONDS.: EI, TEMPPR; ENHANCED (S 15B 2N OT); DATA:MEX2 #722; BASE M/Z: 194; CALI: SSCAL910917 #1; RIC: 3768.

Figure 21:
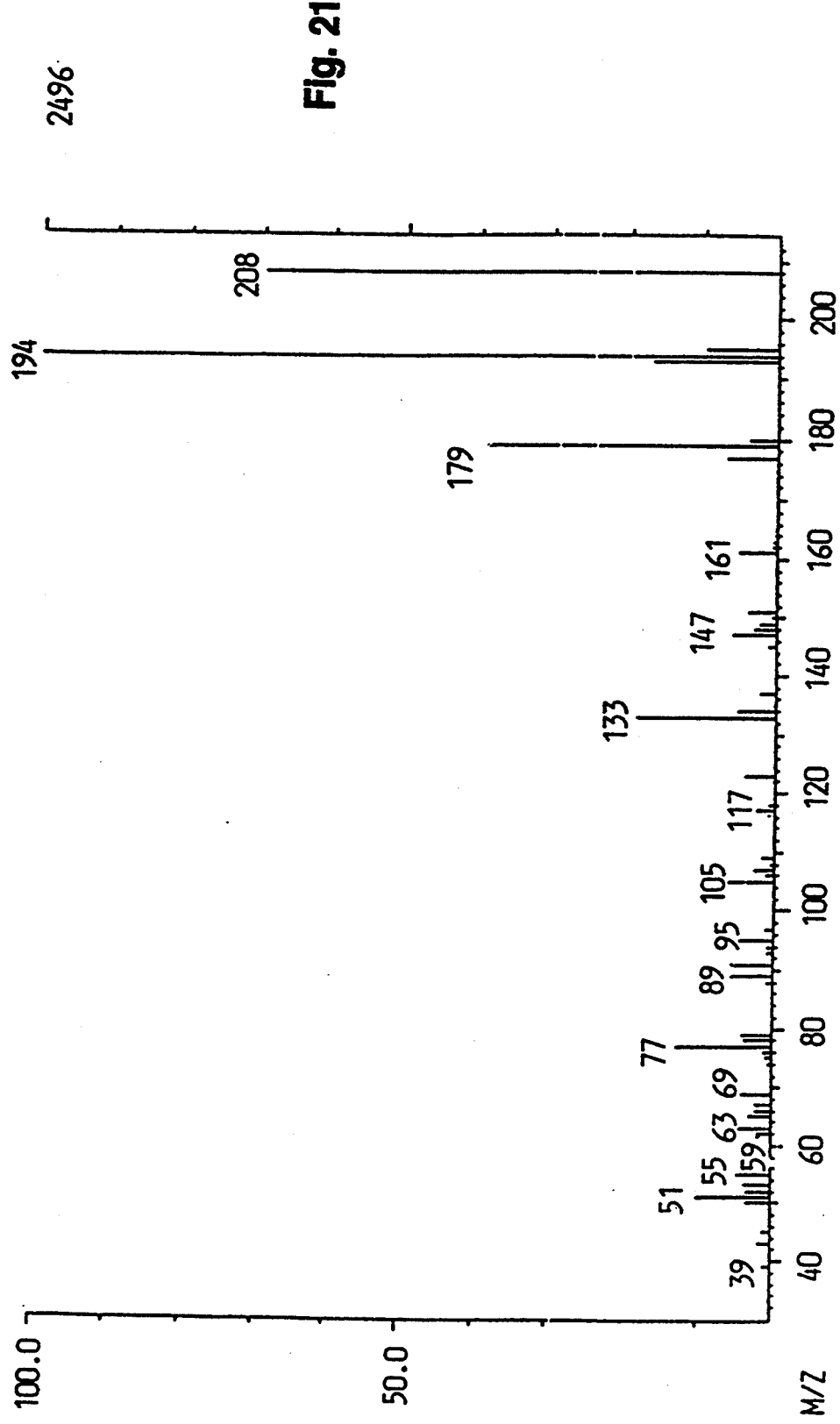

Chromatogram information for FIG. 21 is MASS SPECTRUM; Nov. 17, 1991 16:01:00+14:54; SAMPLE: PRP C; CONDS.: EI, TEMPPR; ENHANCED (S 15B 2N OT); DATA:MEX2 #745; BASE M/Z: 194; CALI: SSCAL910917 #1; RIC: 10112.

Figure 22:
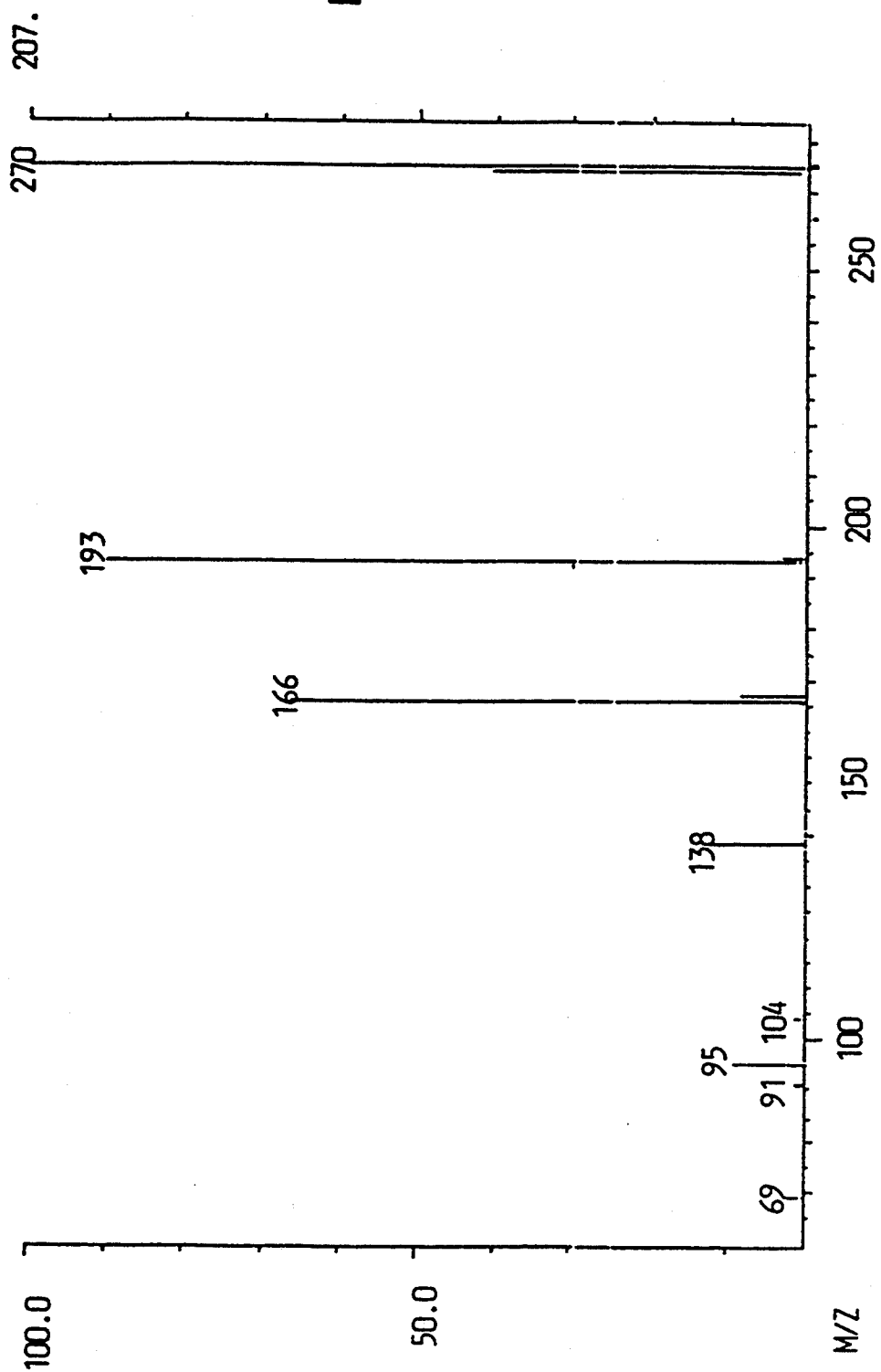

Chromatogram information for FIG. 22 is MASS SPECTRUM; Nov. 17, 1991 16:01:00+18:52; SAMPLE: PRP C; CONDS.: EI, TEMPPR; ENHANCED (S 15B 2N OT); DATA:MEX2 #943; BASE M/Z: 270; CALI: SSCAL910917 #1; RIC: 692.

Figure 23:
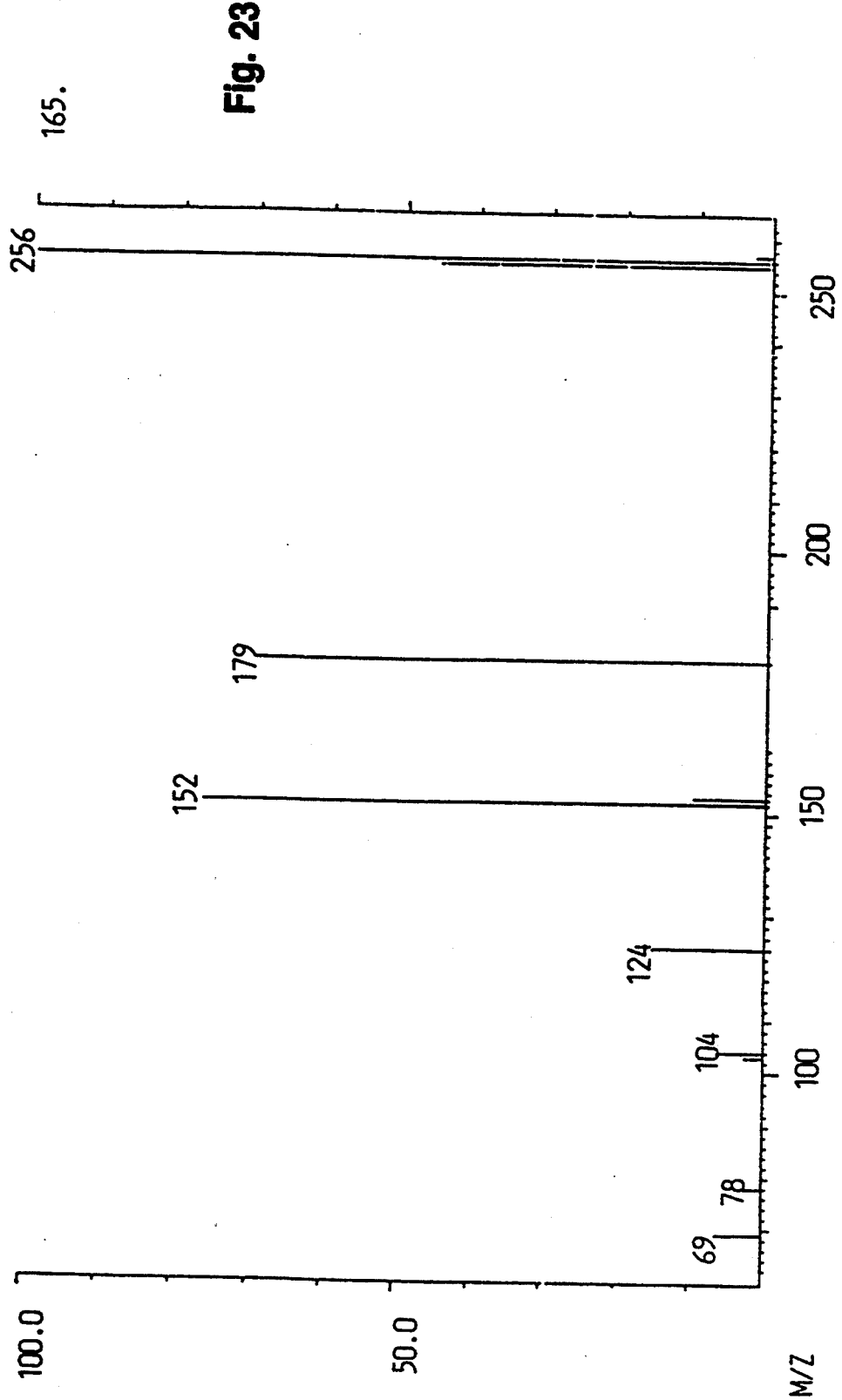

Chromatogram information for FIG. 23 is MASS SPECTRUM; Nov. 17, 1991 16:01:00+19:34; SAMPLE: PRP C; CONDS.: EI, TEMPPR; ENHANCED (S 15B 2N OT); DATA:MEX2 #978; BASE M/Z: 256; CALI: SSCAL910917 #1; RIC: 555.

Figure 24:
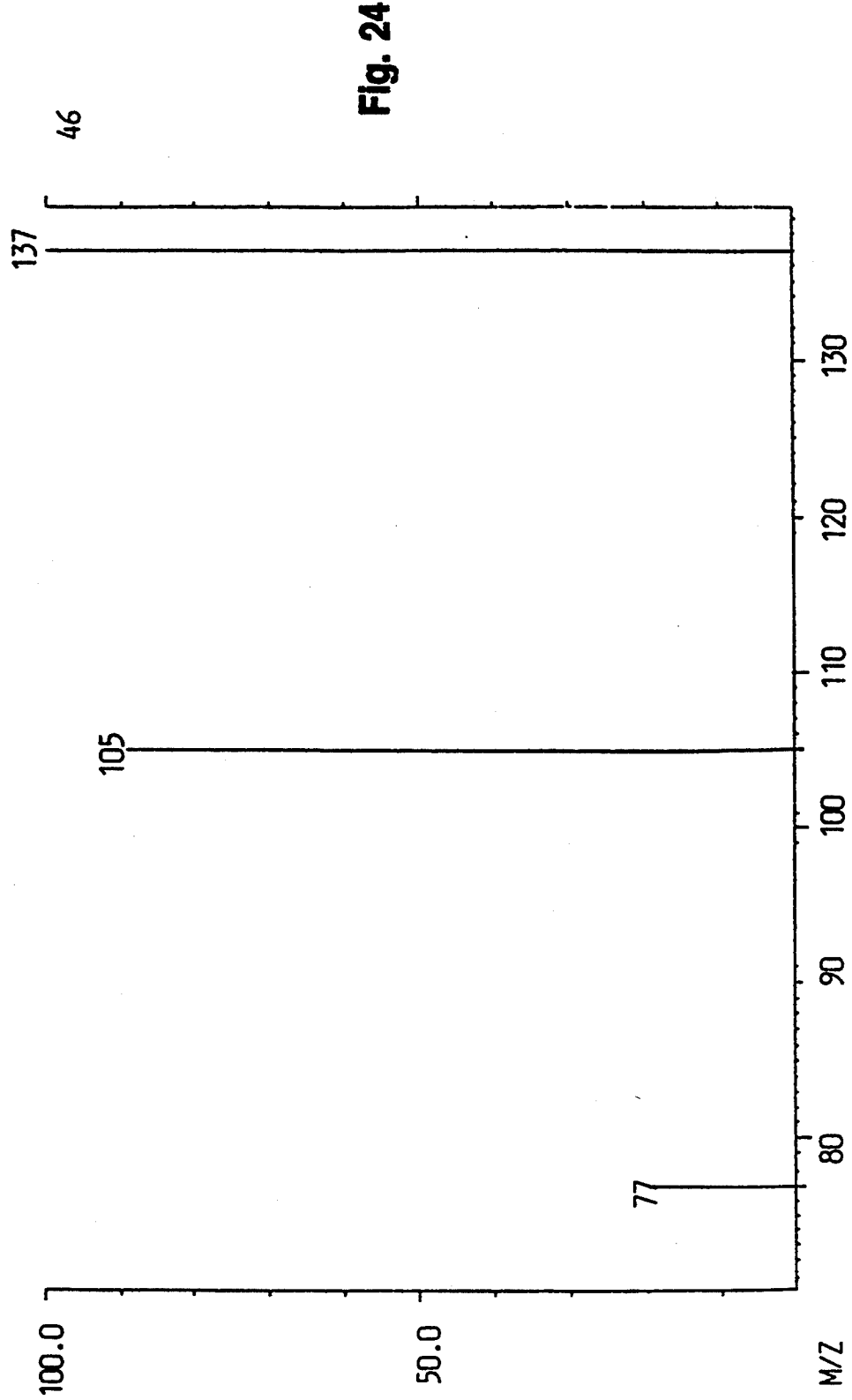

Chromatogram information for FIG. 24 is MASS SPECTRUM; Nov. 17, 1991 16:01:00+19:46; SAMPLE: PRP C; CONDS.: EI, TEMPPR; ENHANCED (S 15B 2N OT); DATA:MEX2 #988; BASE M/Z: 137; CALI: SSCAL910917 #1; RIC: 96.

Figure 25:
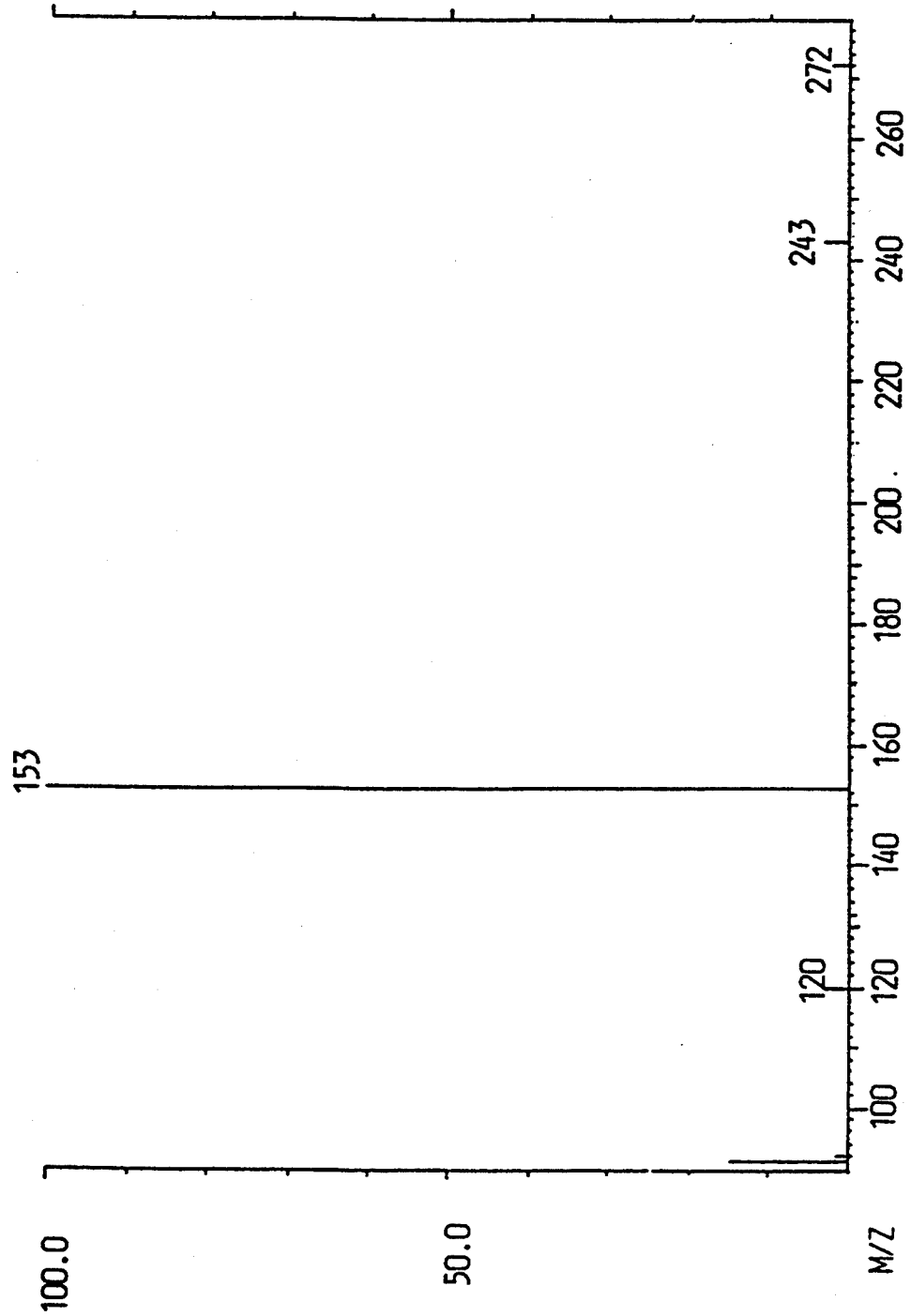

Chromatogram information for FIG. 25 is MASS SPECTRUM; Nov. 17, 1991 16:01:00+20:07; SAMPLE: PRP C; CONDS.: EI, TEMPPR; ENHANCED (S 15B 2N OT); DATA:MEX2 #1006; BASE M/Z: 153; CALI: SSCAL910917 #1; RIC: 218.

Figure 26:
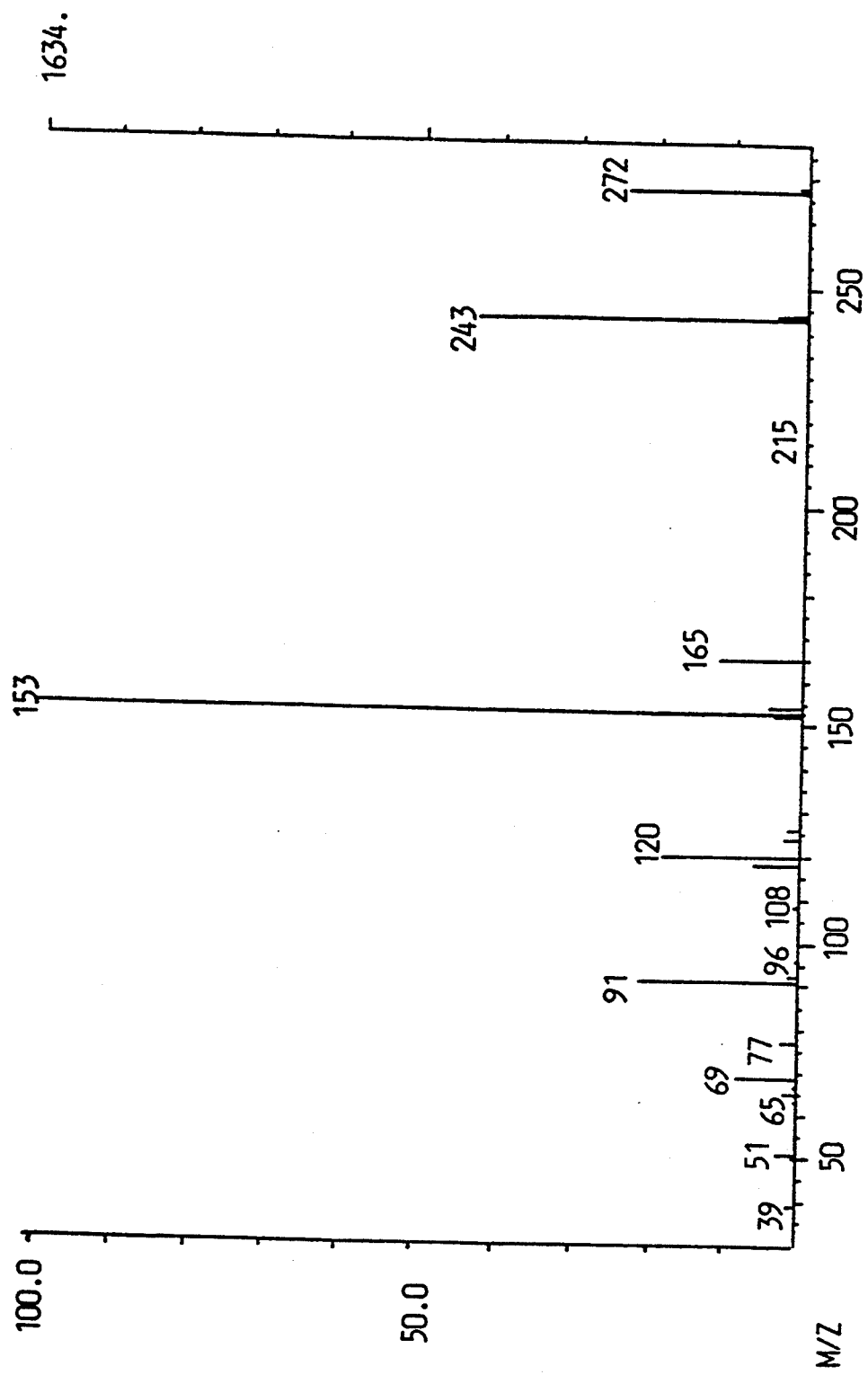

Chromatogram information for FIG. 26 is MASS SPECTRUM; Nov. 17, 1991 16:01:00+20:22; SAMPLE: PRP C; CONDS.: EI, TEMPPR; ENHANCED (S 15B 2N OT); DATA:MEX2 #1018; BASE M/Z: 153; CALI: SSCAL910917 #1; RIC: 4312.

Figure 27:
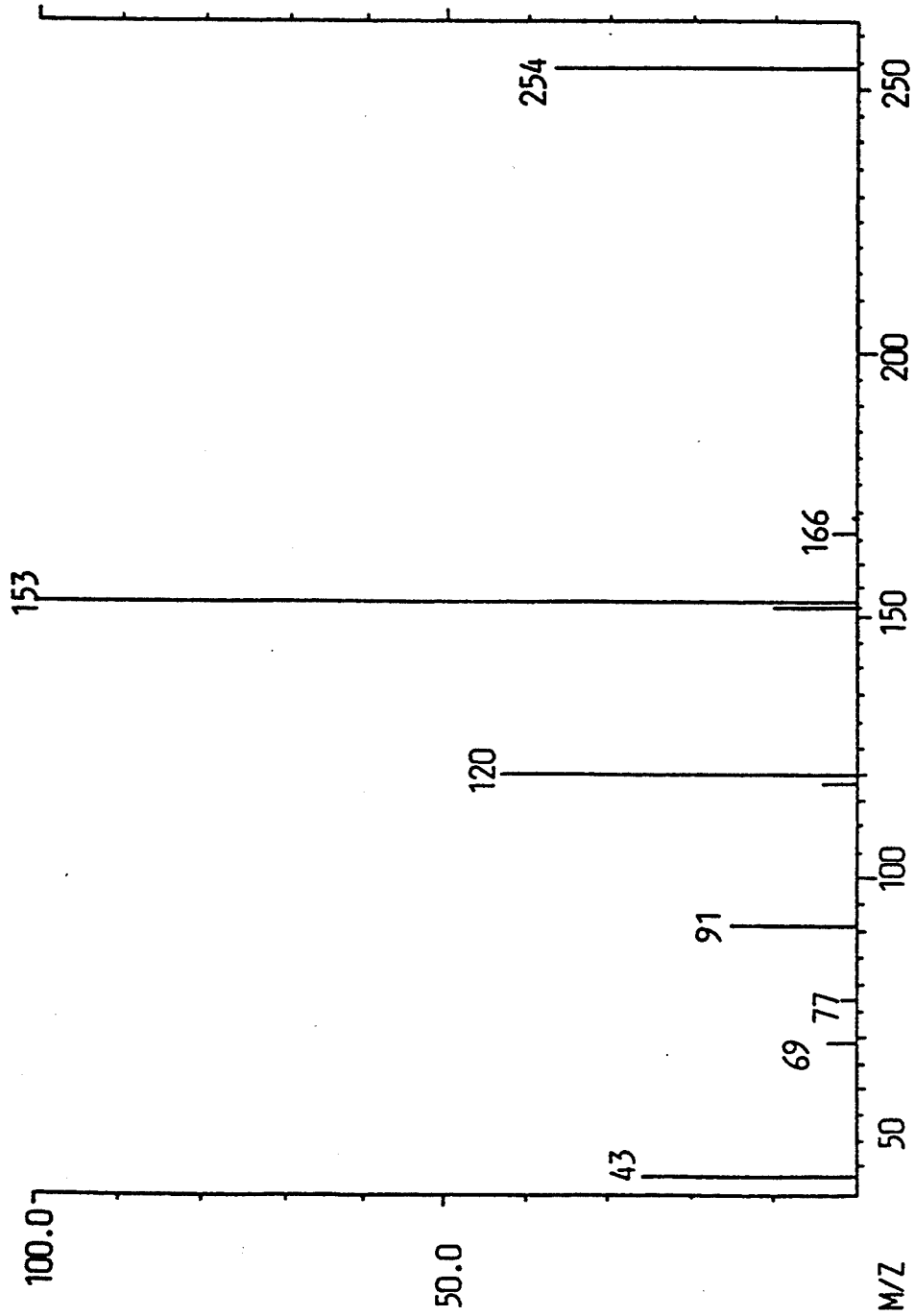

Chromatogram information for FIG. 27 is MASS SPECTRUM; Nov. 17, 1991 16:01:00+21:01; SAMPLE: PRP C; CONDS.: EI, TEMPPR; ENHANCED (S 15B 2N OT); DATA:MEX2 #1051; BASE M/Z: 153; CALI: SSCAL910917 #1; RIC: 471.

Figure 28:
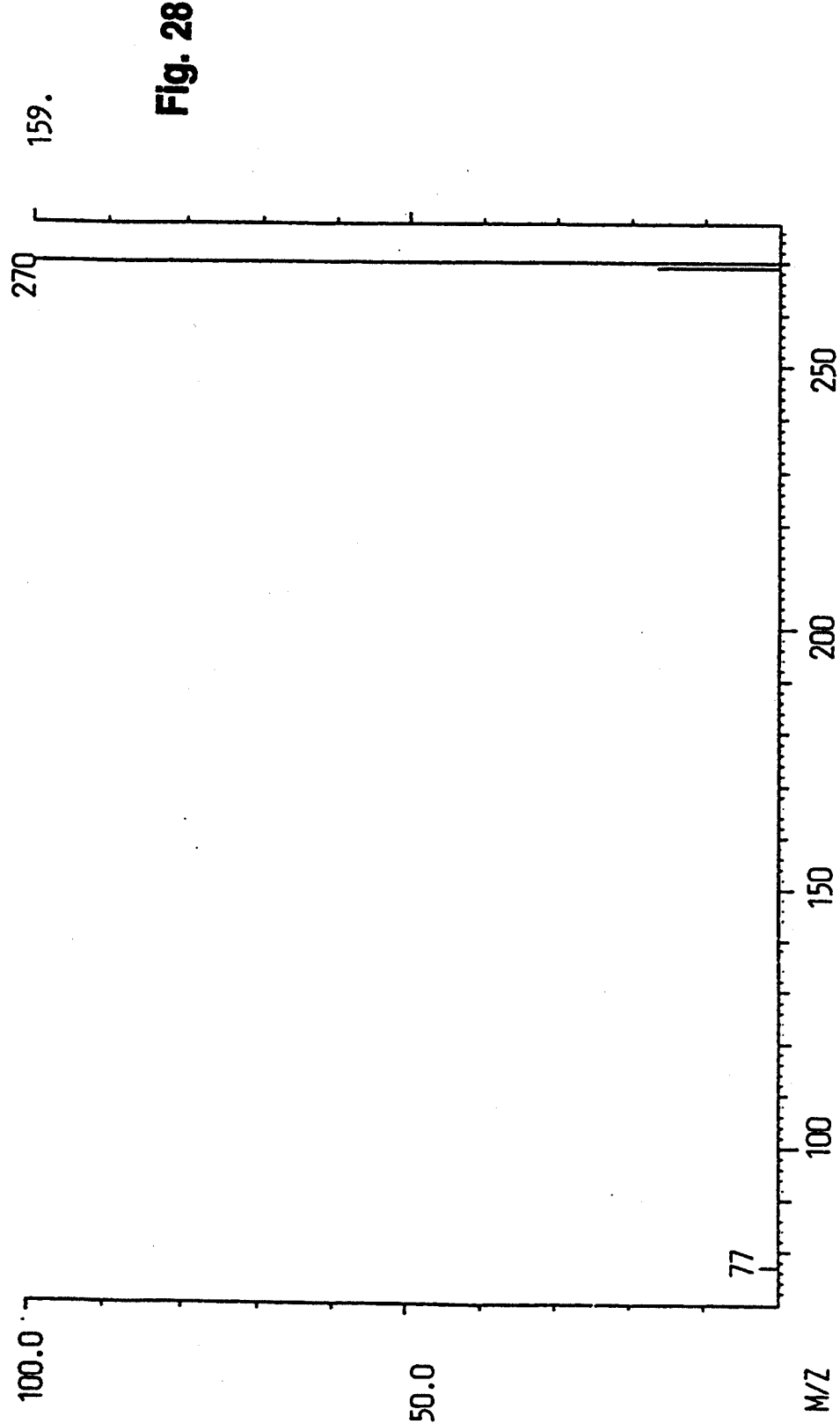

Chromatogram information for FIG. 28 is MASS SPECTRUM; Nov. 17, 1991 16:01:00+21:26; SAMPLE: PRP C; CONDS.: EI, TEMPPR; ENHANCED (S 15B 2N OT); DATA:MEX2 #1072; BASE M/Z: 270; CALI: SSCAL910917 #1; RIC: 189.

Figure 29:
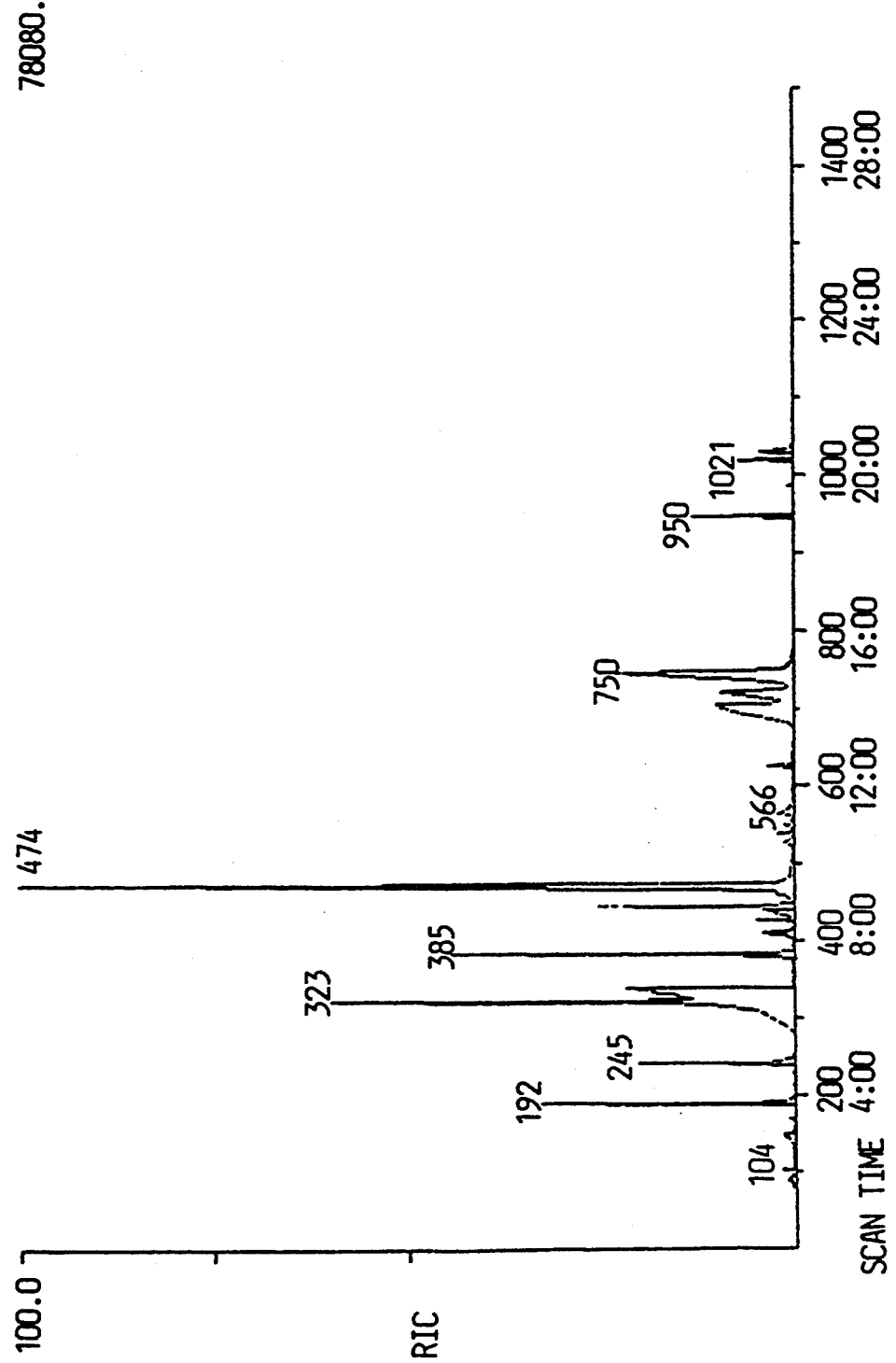

FIG. 29 is the total ion chromatogram with the inner standard. Chromatogram information for FIG. 29 is RIC; Nov. 19, 1991 1:38:00; SAMPLE: PRPC MED INTSTAND; CONDS.: EI, TEMPPR; RANGE: G 1,1500; LABEL: N O, 4.0; QUAN: A 0, 1.0 J O; BASE: U20, 3; DATA:MEX7 #1; SCANS 1–1500; CALI: SSCAL910917 #1.

Figure 30:
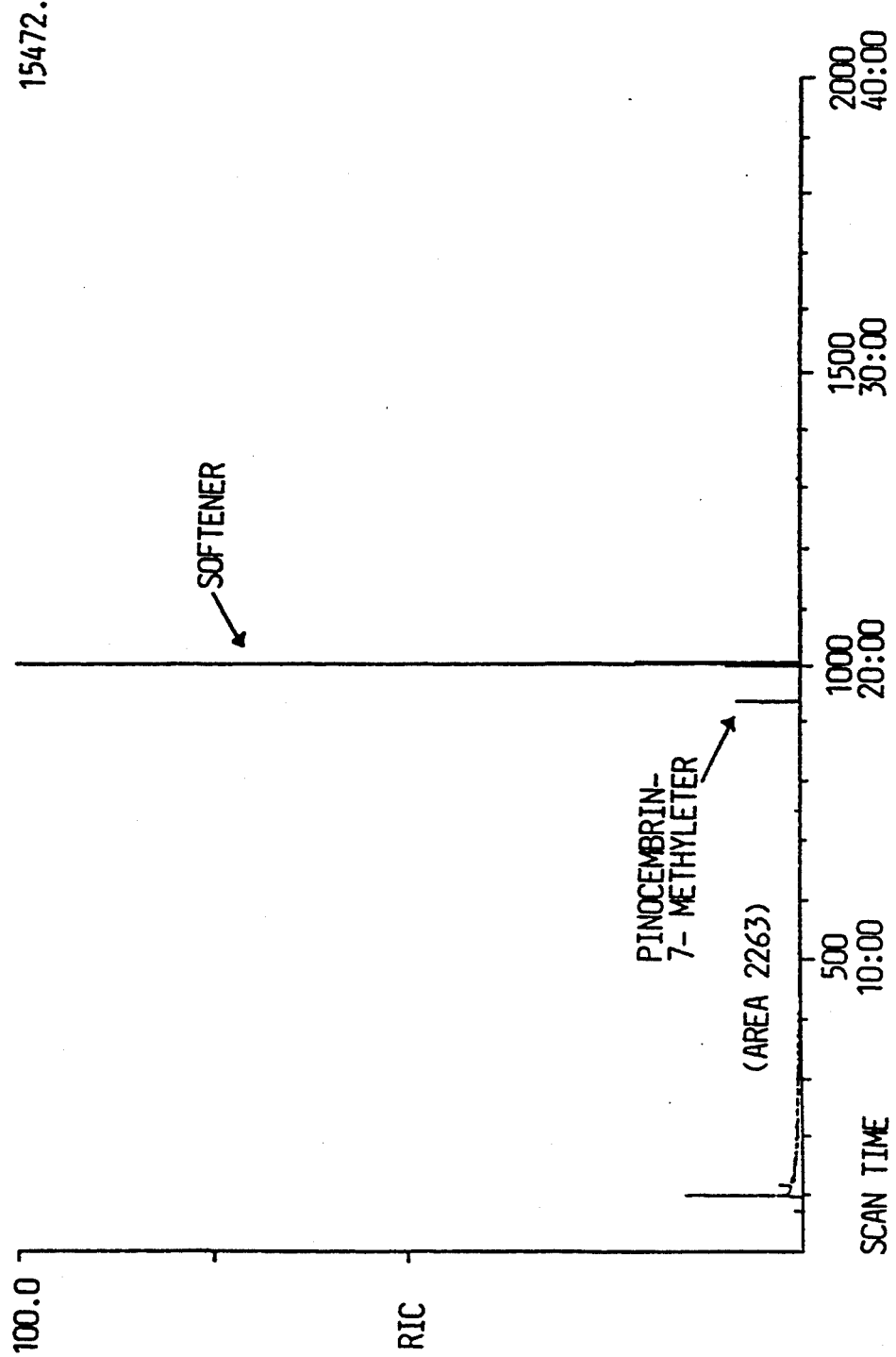

FIG. 30 is the total ion chromatogram of the inner standard. Chromatogram information for FIG. 30 is RIC; Nov. 18, 1991 12:04:00; SAMPLE: MEXO; CONDS.: EI, TEMPPR; RANGE: G 1,2000; LABEL: N O, 4.0; QUAN: A 0, 1.0 J O; BASE: U20, 3; DATA:-MEX6 #1; SCANS 1–2000; CALI: SSCAL910917 #1.

Figure 31:
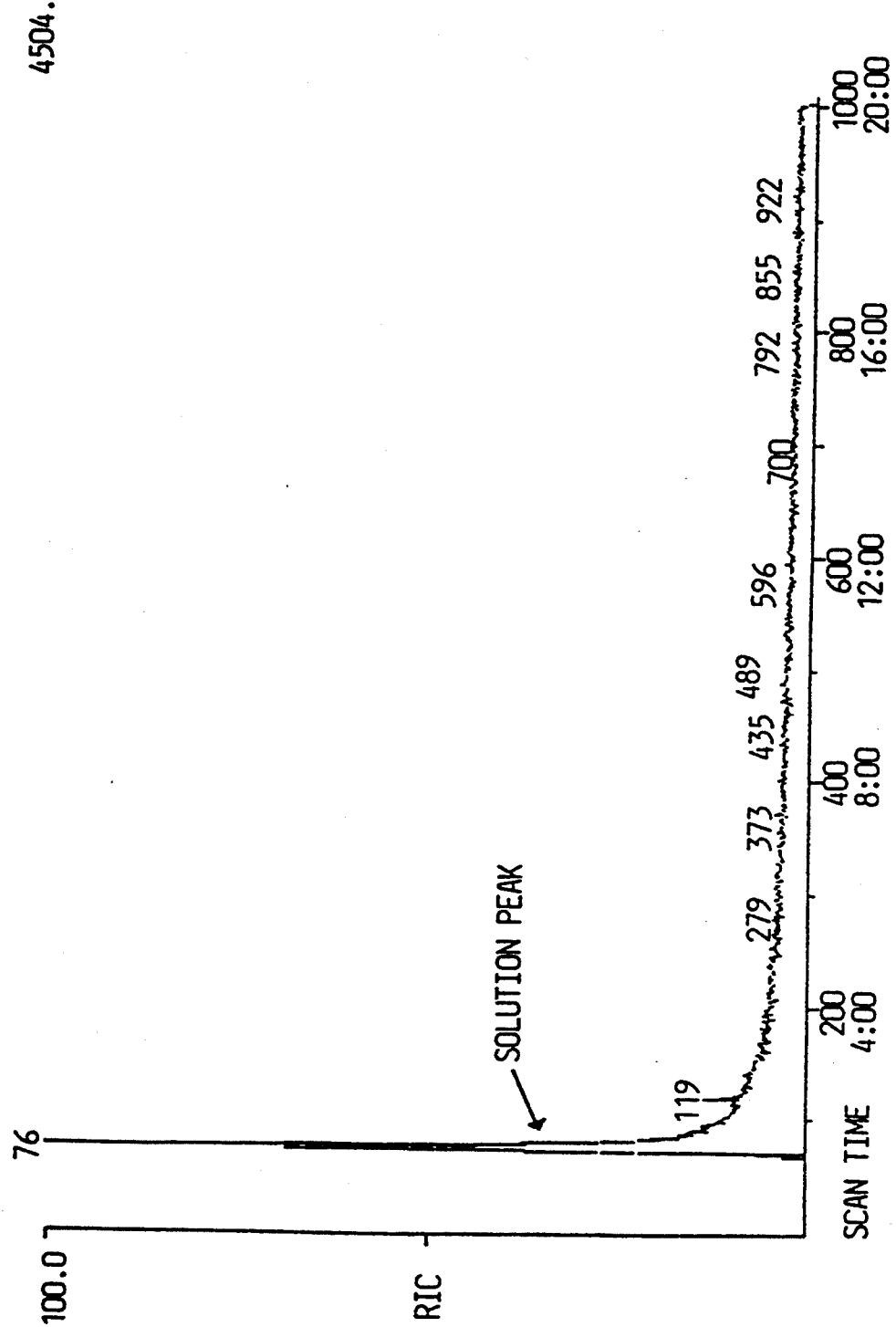

FIG. 31 is the GC-MS of example 5. Chromatogram information for FIG. 31 is RIC; Nov. 17, 1991 16:38:00; SAMPLE: MEXO; CONDS.: EI, TEMPPR; RANGE: G 1,1000; LABEL: N O, 4.0; QUAN: A 0, 1.0 J O; BASE: U20, 3; DATA:MEX3 #1; SCANS 1–1000; CALI: SSCAL910917 #1.

Figure 32:
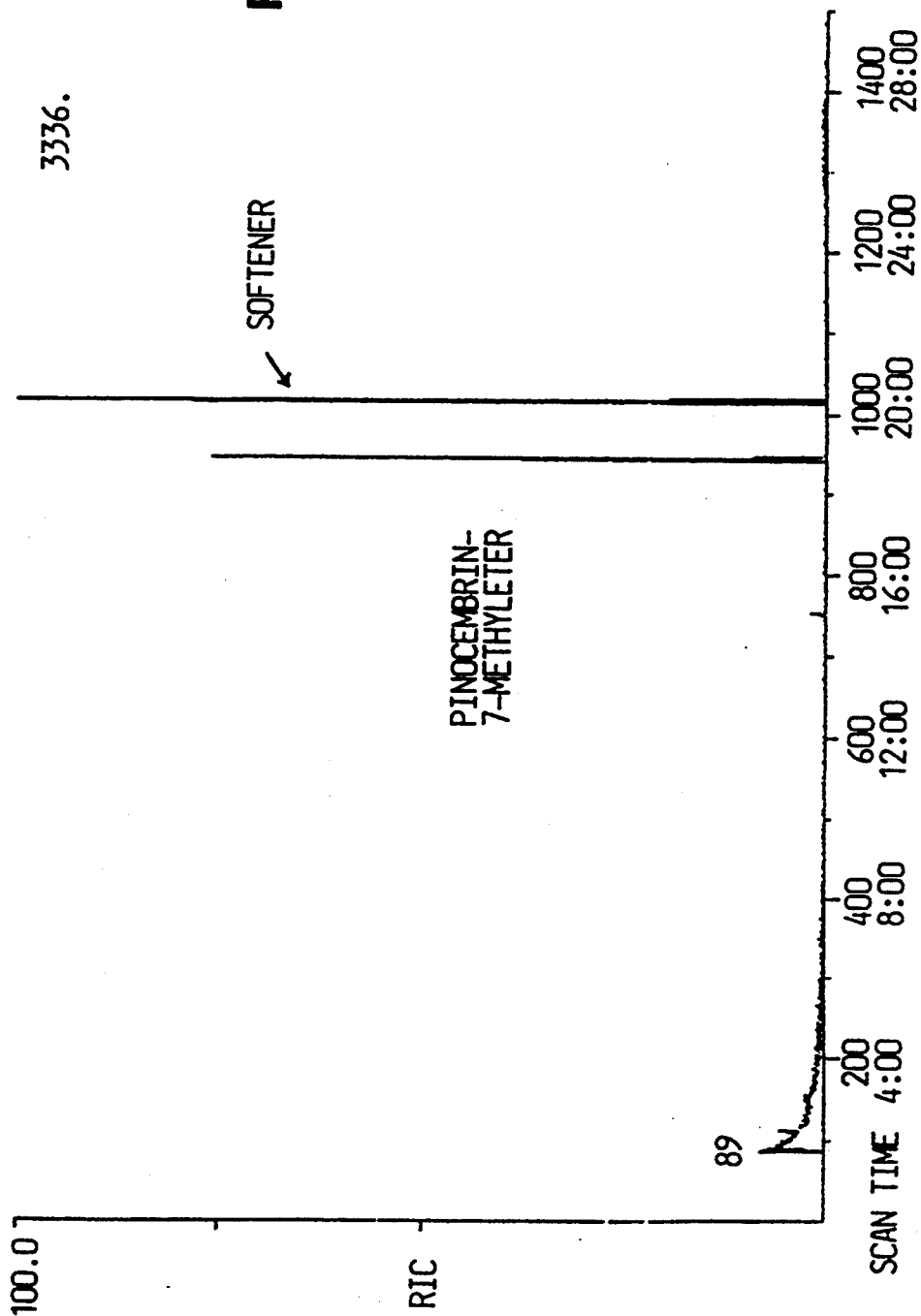

FIG. 32 is the GC/MS of example 5 with inner standard. Chromatogram information for FIG. 32 is RIC; Nov. 19, 1991 2:17:00; SAMPLE: MEXO; CONDS.: EI, TEMPPR; RANGE: G 1, 101; LABEL: N O, 4.0; QUAN: A 0, 1.0 J O; BASE: U20, 3; DATA:MEX8 #1; SCANS 1–1500; CALI: SSCAL910917 #1.

Figure 33:
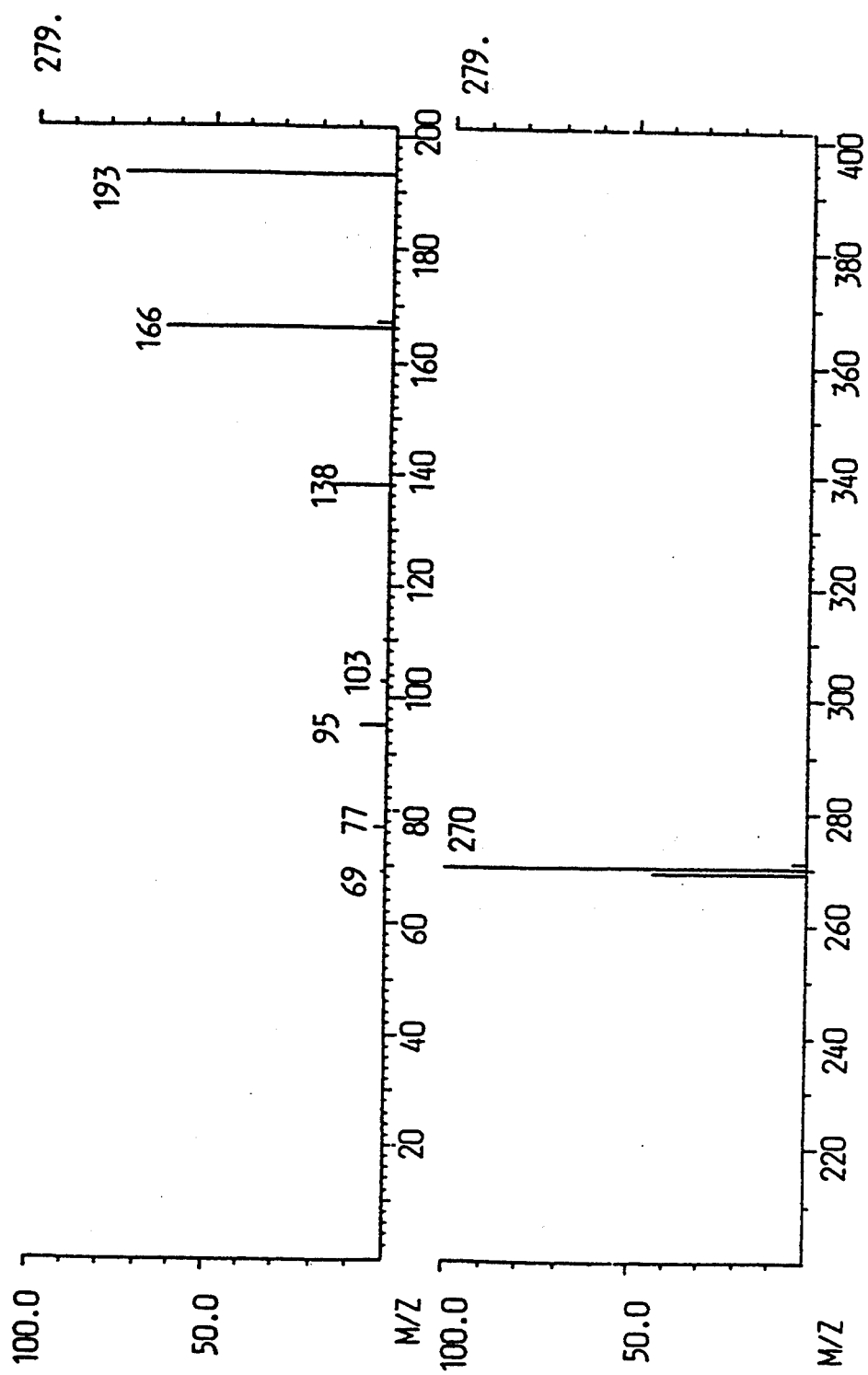

FIG. 33 is the mass spectra of the inner standard. Chromatogram information for FIG. 33 is MASS SPECTRUM; Nov. 18, 1991 12:04:00+18:49; SAMPLE: MEXO: EI, TEMPPR; ENHANCED (S 15B 2N OT); DATA:MEX6 #941; BASE M/Z: 270; CALI: SSCAL910917 #1; RIC: 893; AREA 2263.

Figure 34:
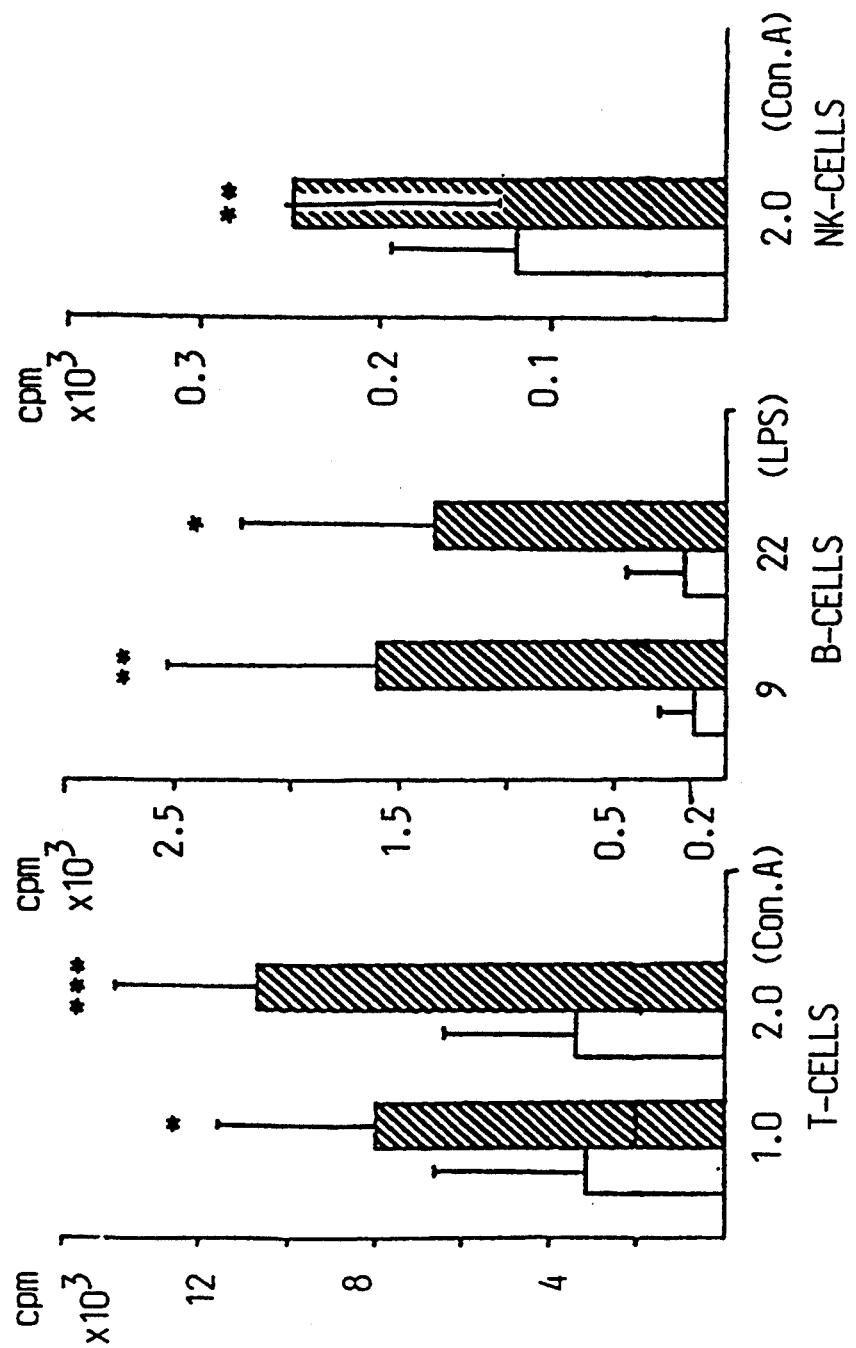

FIG. 34 shows the immune cell activity of T-(Con A) in spleen and thymus and B-cells (LPS) in spleen after propolis treatment in vivo.

Figure 35:
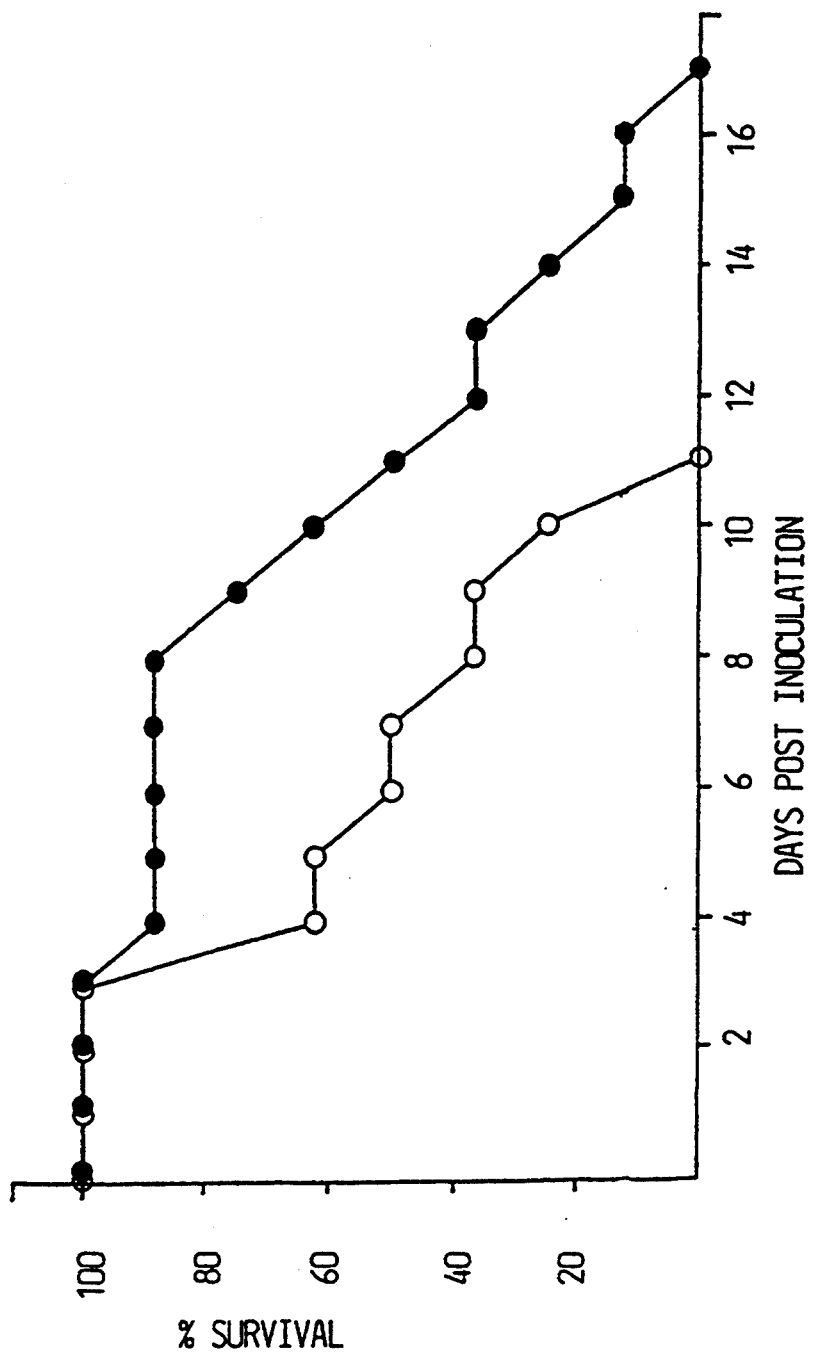

FIG. 35 shows the survival of Coxsackievirus B3 in untreated and propolis treated Balb/c mice. The open circles are CB3 (untreated) and the solid circles are CB3 treated with propolis.

Figure 36A:
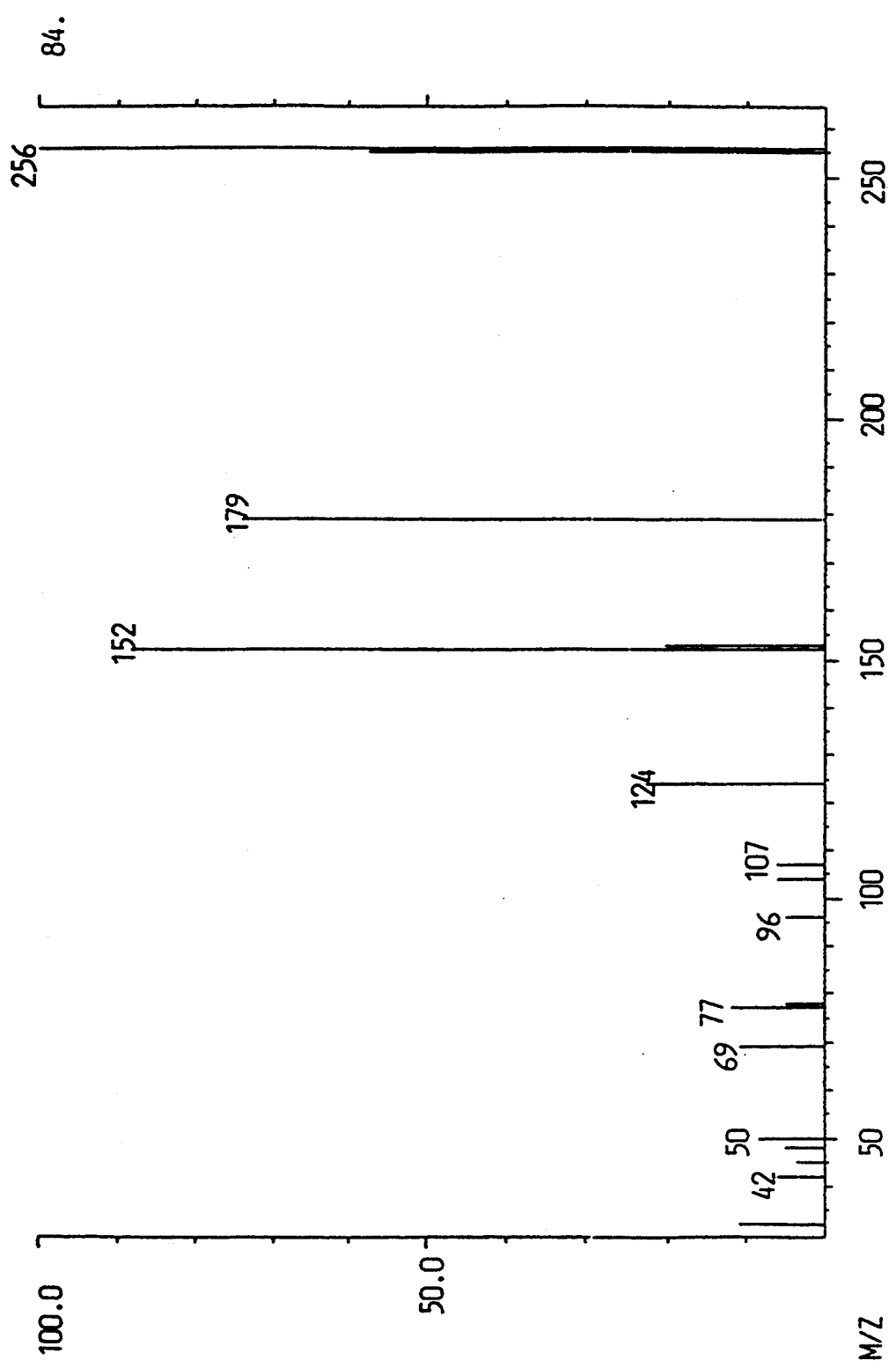
Figure 36B:
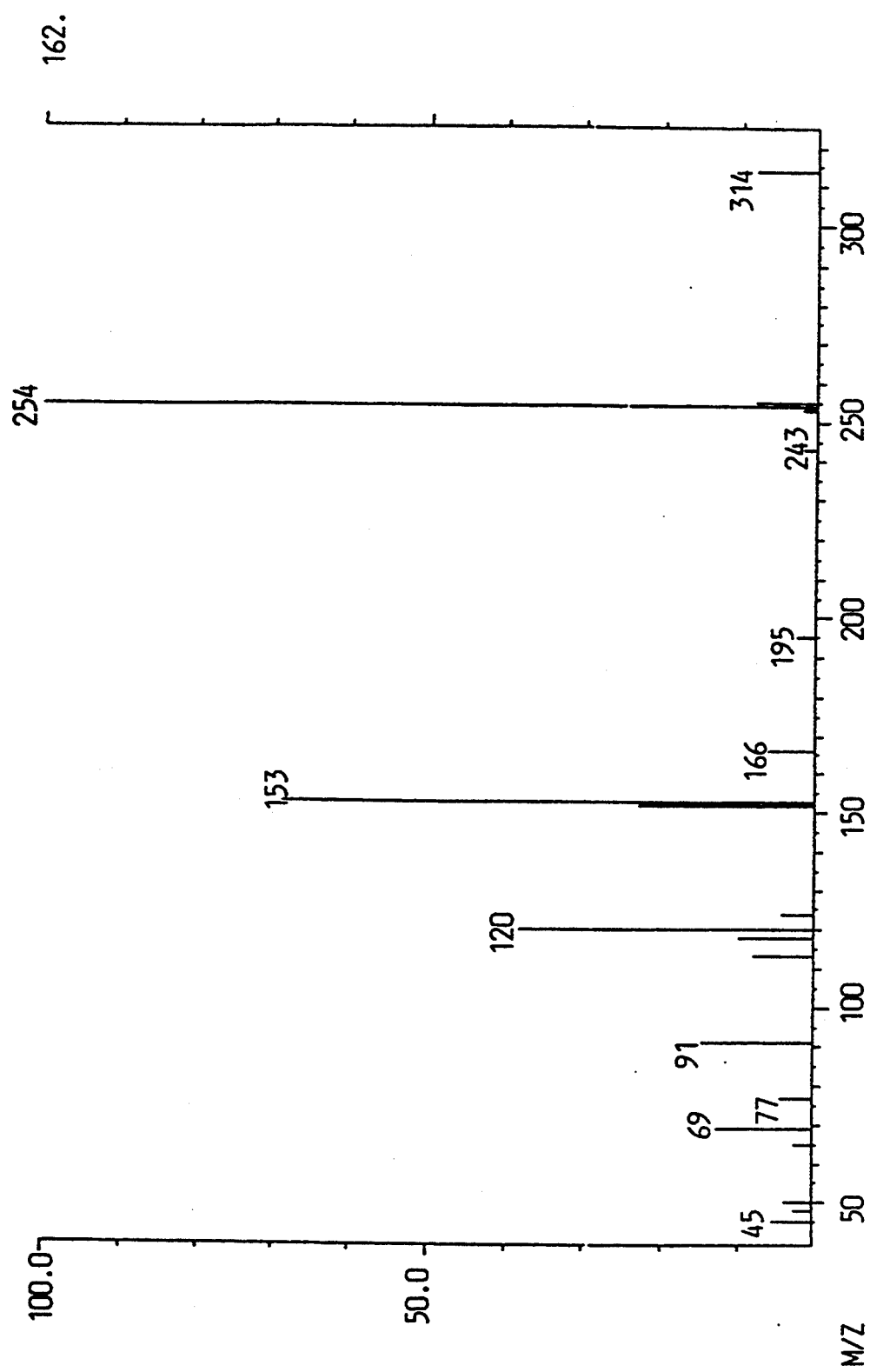

FIGS. 36a and 36b are mass spectra of propolis showing the presence of pinocembrin and pinobanksin-3-acetate, respectively. Chromatogram information for FIG. 36a is MASS SPECTRUM; Dec. 04, 1991 4:27:00+31:52; SAMPLE: PRP-C 70 1, UTAN I.S.; CONDS.: EI 70 EV, FULLSCAN 30–500 1.2 S; ENHANCED (S 15B 2N OT); DATA:MEX1204B #1593; BASE M/Z: 256; CALI: ACCAL911204 #1; RIC: 369. Chromatogram information for FIG. 36b is MASS SPECTRUM; Dec. 04, 1991 4:27:00+34:47; SAMPLE: PRP-C 70 1, UTAN I.S.; CONDS.: EI 70 EV, FULLSCAN 30–500 1.2 S; ENHANCED (S 15B 2N OT); DATA:MEX1204B #1739; BASE M/Z: 254; CALI: ACCAL911204 #1; RIC: 530.

DETAILED DESCRIPTION OF THE INVENTION AND PREFERRED EMBODIMENTS THEREOF

According to the present invention there is used an alcoholic solution containing propolis. This alcoholic solution is added to a water solution containing 0.1–17 weight % of NaCl with a temperature of 30°–95° C. for 10 to 20 hours, whereafter the solution is freed from bottom sediment.

The alcohol may be an alcohol containing 1–20 carbon atoms, preferably 1–5 carbon atoms, such as methanol, ethanol, propanol, butanol, especially ethanol. Preferably there is used an ethanolic propolis solution prepared according to German patent 88109824.8. According to this patent, a mixture of the substances with formula I can be prepared from a propolis extract by extracting propolis in a closed system at a low temperature, 0°–20° C. with an ethanol/water mixture at a volume ration of 87:13 under ultrasonic treatment from 18–25 kHz for a short period such as 25 minutes, the resultant suspension being decanted and the clear propolis extract freed from the solid particles. Preferably the propolis is ground to a particle size of 3 mm diameter before extraction using a suitable mill into fine particles (max. diameter of 5 mm). The disclosure of German patent no. 88109824.8 is hereby incorporated by reference.

The alcoholic solution of propolis is preferably added to the NaCl solution in an amount of 1–60% by volume based on the sum of the volumes of the two solutions.

The propolis solution is preferably added to the NaCl-solution drop by drop over about 1–7 hours, preferably 5 hours. A brown sediment is formed. The mixture is kept at 30°–95° C. for another 5–100 hours, preferably about 40–80 hours. A temperature of 50°–70° C. is preferred, preferably 60° C. A light yellow solution is formed over a hard, dark brown sediment. The propolis solution being alcoholic is evaporated during the process and the yellow extract that is obtained has about the same volume as the NaCl solution used.

The substances and the compositions according to the invention can be used as antimicrobial agents for human or veterinary use. They can be used for prophylaxis or treatment of inflammations or infections caused by Gram-positive or Gram-negative bacteria, viruses and fungi. The substances or mixtures thereof can be used as fodder, food-stuffs, hygienic articles, medicines and natural medicines. Clinical studies in Sweden have also shown the extract according to the invention to be useful as an antiseptic and analgesic, and to improve the healing process of wounds.

Tests discussed below also show that the extract according to the invention can be used effectively against bacteria causing gastric ulcer and vaginal infections.

The extract can also be used for preparing containers and tools for fodder and food-stuffs and for treatment of surgical instruments, dental instruments, cosmetic tools such as syringes, bandages, plasters, dressings, compresses, and rinsing solutions. Further, they can be used for treating all sorts of spaces such as operating rooms, rooms where animals are kept, and places for preparing or storing foods and fodder. Having immune stimulating activity, they can also be used in vaccines as adjuvants.

Use of the extraction process according to the invention results in a sodium chloride solution containing pinocembrin and pinobanksin-3-acetate. FIGS. 36a and 37a show representative mass spectra of propolis extracted according to the invention. The extract can be adjusted to contain preferably a physiological solution of 0.6–0.9%, preferably 0.9% NaCl. This is very suitable for treating or preventing mastitis, i.e., inflammation in the udder. The saline extract may be prepared under sterile conditions and injected directly into the udder. PROVET TM (which is used today for the same purpose contains crude propolis (from Apipharm Co. Ltd.), Lanacolum, alcohol-cetyle-stearate, polyoxyethylene-sorbitan-monolaurate, vaseline, and paraffin. PROVET TM, however, must be introduced in the milk canal of each teat of the diseased mammal at the end of milking. PROVET TM thus consists of four disposable syringes for injection in each of the teats. Thus, the composition according to the invention is easier to administer than the prior products.

When tested as 1–10% nose spray in a total of 58 patients, no local or systemic allergic reactions were observed in the patients.

The substances and the compositions according to the invention can be used in any pharmaceutical form such as tablets, capsules, solutions for injections, solutions or spray for nasal treatment.

The administration forms may contain pharmaceutically acceptable carriers such as one or more compatible solid filler diluents or solid or liquid substances added to aid in the production of the pharmaceutical forms, such as lubricants to reduce friction and glidants to improve flow of the particulate mixtures. By "compatible" as used herein is meant that the components are capable of being commingled without interacting in a manner which would substantially decrease the pharmaceutical efficacy.

Some examples of substances which can serve as pharmaceutical carriers are sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate, zinc stearate; calcium sulfate; silicon dioxide; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; and alginic acid; as well as other non-toxic compatible substances used in pharmaceutical formulations. Wetting agents such as sodium lauryl sulfate, as well as coloring agents, lubricants, excipients, stabilizers, antioxidants, and preservatives, can also be present.

For nasal treatment, there can be used a physiological NaCl solution containing 0.9% by weight NaCl and 1–20% propolis extract. For treatment of mastitis there can be used a 0.9% NaCl solution containing 20–50% propolis extract, preferably about 30%.

Reference herein to a % propolis extract means the volume of the starting alcoholic propolis solution in relation to the sum of the propolis and NaCl solutions. Thus, the end product of Example 2 is considered to contain 30% propolis extract.

The features and advantages of the present invention will be more clearly understood by reference to the following examples, which are not to be construed as limiting the invention.

EXAMPLES

Example 1

In the extraction vessel, 500 liters of an ethanolic solution not less than 87% by weight in water is prepared. While the mixture is being stirred, 20 kg of the ground propolis is added to the contents of the extractor. The batch is subjected to ultrasonic extraction (18–25 kHz) for 25 minutes, then left for two hours, decanted and filtered.

The filtration is effected via a pressure filter with rapid filter-paper inserts. The clear propolis extract obtained is reduced to the required concentration of 5–80% of the dry substance in a column concentrator in a 150–50 mm $H_2O$ vacuum by means of a heat pump. The concentration is performed at a temperature of no greater than 20° C.

Example 2

The extract obtained in Example 1 is diluted to contain a dry substance weight of 10% in alcohol. NaCl is dissolved in distilled water to a concentration of 0.9%. 700 ml of the solution is placed in a beaker which is put into a water bath. The temperature in the beaker is kept at 30° C. 300 ml of the propolis extract containing 10 weight % propolis in ethanol is added drop by drop to the NaCl over about a 5 hour period. A muddy brown precipitate is obtained. The temperature of the solution is controlled by keeping the water bath boiling and by continuously adding water for 15 hours to keep the water level. By then a light yellow solution is formed in a volume of about 700 ml, with the rest of the solution evaporated during the heating. The beaker containing the solution is left in the water bath until the contents have reached room temperature. The precipitate is separated from the solution. Analysis of the yellow solution with mass spectra shows that it contains pinocembrin and pinobanksin-3-acetate.

Example 3

The extract obtained in Example 1 is diluted to contain a dry substance weight of 10% in ethanol. NaCl is dissolved in distilled water to a concentration of 10%.

700 ml of the solution is placed in a beaker which is placed in a water bath. The temperature of the beaker is kept at 30° C. 300 ml of the propolis extract containing 10 weight % propolis in ethanol is added drop by drop to the NaCl solution for about five hours. A muddy brown precipitate is obtained. The temperature of the solution is controlled by keeping the water bath boiling and by continuously adding water for 15 hours to keep the water level constant. A light yellow solution having a volume of about 700 ml is formed, with the rest of the solution evaporating during heating. The beaker containing the solution is left in the water bath until the contents have reached room temperature. The precipitate is separated from the solution.

Example 4

The extract obtained in Example 1 is diluted to contain a dry substance weight of 10% in ethanol. NaCl is dissolved in distilled water to a concentration of 15%. 700 ml of the solution is placed in a beaker which is placed in a water bath. The temperature of the beaker is kept at 30° C. 300 ml of the propolis extract containing 10 weight % propolis in ethanol is added drop by drop to the NaCl solution for about five hours. A muddy brown precipitate is obtained. The temperature of the solution is controlled by keeping the water bath boiling and by continuously adding water for 15 hours to keep the water level constant. A light yellow solution having a volume of about 700 ml is formed, with the rest of the solution evaporating during heating. The beaker containing the solution is left in the water bath until the contents have reached room temperature. The precipitate is separated from the solution.

Example 5

The procedure of Example 2 is repeated but with 800 ml of the NaCl solution and 200 ml of the propolis extract. The resultant solutions are analyzed by mass spectroscopy as follows. Two ml of the yellow extract are extracted with 2 ml ethyl acetate. Volumes of 1 and 5 microliters of the ethyl acetate phase are injected into a gas chromatograph coupled to a Jeol 300 mass spectrometer. The gas chromatograph comprises a 15 m long capillary column with unpolar stationary phase. Splitless injection is made 1 minute 240°, temperature processing; 45°, 1 minute 10° per minute The mass spectrometry analysis parameters are EI 70 EV 1.2 seconds/scan from mass 35 to 300. The inner standard is added to the sample with 40 ul of 0.7 ug/ml of pinocembrin-7-methyl ether before the extraction was performed.

The inner standard pinocembrin-7-methyl ether is also present in the sample, which makes analysis difficult. In order to be able to use the inner standard, the sample is chromatographed with and without inner standard so that the interference by the inner standard may be subtracted. Pinocembrin and pinobanksin-3-acetate are identified with reference spectra.

The results are shown in FIGS. 3–33. Chromatogram 1 (FIG. 3) shows the total ion chromatogram. Chromatogram 2 (chromatograms 2:1 to 2:25) (FIGS. 4–28) is the mass spectra for all peaks from the analysis of chromatogram 1 with the identity of the peak of chromatogram 1 which was chromatographed for chromatograms 2:1 to 2:25 (FIGS. 4–28) being shown at the upper center of each these chromatograms. Chromatogram 3 (FIG. 29) is the total ion chromatogram with the inner standard. Chromatogram 4 (FIG. 30) is the total ion chromatogram of the inner standard. Chromatogram 5 (FIG. 31) is the GC-MS of example 5. Chromatogram 6 (FIG. 32) is the GC-MS of example 5 with inner standard; and chromatogram 7 (FIG. 33) is the mass spectra of the inner standard. The control spectra does not contain any substances soluble in ethyl acetate.

These results show that 2 ml of the extract, which is a 0.9% NaCl solution, contains 200 ng/ml ($20 \times 10^{-8}$ g/ml) of pinocembrin and 90 ng/ml ($90 \times 10^{-9}$ g/ml) of pinobanksin-3-acetate. There are no other detectable components in the extract.

Example 6

The procedure of Example 2 is repeated but with 770 ml of the NaCl solution and 230 ml of the propolis extract.

Example 7

The procedure of Example 2 is repeated but with 500 ml of the NaCl solution and 500 ml of the propolis extract.

The light yellow solution is further purified by dialysis against water. 50 ml of the extract is dialyzed against 250 ml of distilled water through a dialysis tube (Model mw cataf 3500, Kebo AB, Sweden).

Both the undialyzed and the dialyzed solution are tested by mass spectra with Solid Probe/$\mu$s using standard techniques. One $\mu$l of a mixture of the test solution and 96% p.a. ethanol 1:1 is evaporated at about 60° C, chilled to 25° C. and then heated 10° C./second to 375° C., which temperature is maintained for about 4 minutes. Mass spectra from m/2 41–641 with 1 second cycles are taken during this period.

The mass spectra of the dialyzed product are shown in FIG. 1. FIG. 1a shows the temperature ramp, the four regions A–D and the total ion stream. FIG. 1b shows the total ion stream after a numerical filter. FIG. 1c shows the spectrum in the region A, FIG. 1d the spectrum of region B, FIG. 1e the spectrum of region C and FIG. 1f the spectrum of region D, respectively. FIGS. 2a–2f show the same spectra for the undialyzed product. The mass spectra show that the product contains pinocembrin and pinobanksin-3-acetate.

Example 8

The procedure of Example 2 is repeated but after adding the propolis extract drop by drop to the NaCl solution, the mixture is heated at 60° for 48 hours. The yellow extract is separated from the precipitate and analyzed. Analysis of the yellow solution with mass spectra shows that it contains pinocembrin and pinobanksin-3-acetate.

Example 9

The procedure of Example 2 is repeated but after adding the propolis extract drop by drop to the NaCl solution, the mixture is heated at 60° for 48 hours. Analysis of the yellow solution with mass spectra shows that it contains pinocembrin and pinobanksin-3-acetate.

Example 10

The starting material is prepared as described in Example 1, and the clear propolis extract is reduced to a concentration of 20 weight %. Thereafter, the procedure of Example 2 is repeated, but after adding the propolis extract drop by drop to the NaCl solution, the mixture is heated at 60° for 72 to 78 hours. Analysis of the yellow solution with mass spectra shows that it contains pinocembrin and pinobanksin-3-acetate. This extract is suitable as an antiviral agent, for example, through stimulation of the immune system (see Example 14).

Example 11

The following strains are tested: *Klebsiella oxytoca* (K1), *Pseudomonas aeruginosa* (P.a.), a coagulase-negative staphylococcus (SK-), *Streptococcus uberis* (Sru), *Streptococcus agalactiae* (Sra), *Proteus mirabilis* (P.m), *Actinomyces pyogenes* (A.p.), *Saccharomyces cerevisiae* (S.ce), and *Candida pseudotropicalis* (C.ps) (*Kluveromyces marxianus*). Bovine mastitis is often caused by *Staphylococcus aureus*, coagulase-negative staphylococci, *Streptococcus agalactiae*, *Streptococcus dysgalactiae* and *Streptococcus uberis*. In addition, mastitis (both rapidly blazing mastitis and sub-clinical mastitis) may also be caused by the other listed microorganisms. Mastitis may be treated with penicillin, but increasing bacterial resistance to penicillin has proved a problem.

The four propolis solutions are negative at sterility control tests made before the growth tests. All strains are tested at once, and are cultivated in bovine broth at 37° C. for 20 hours to yield $10^6$–$10^9$ microorganisms per ml (see Table I).

Samples of 0.1 ml are taken from each broth (dilution of $10^2$ or $10^3$) and added to 0.9 ml of the extract according to example 2 or 5 so that each mixture contains $10^2$–$10^5$ bacteria per ml (see Table II). The solutions are then incubated at 38° C. After 0 and 3 hours the bacteria are counted. The results are given in Tables III–IV. After cultivation for three hours, there were no viable bacteria, yeast or fungi in the culture, which indicates that every type of microorganism was dead after incubation three hours in the tested extracts prepared according to Examples 2 and 5.

Example 12

The following three strains are analyzed in another test: *Staphylococcus aureus*, *Streptococcus dysgalactiae*, and *Escherichia coli*.

All propolis solutions are checked for existence of viable bacteria, and are all found to be free from bacteria.

The bacteria are cultivated for 24 hours so that the bacterial solutions contain $10^7$–$10^8$ bacteria per ml. From every broth culture, 0.1 ml is taken out and mixed with 0.9 ml propolis solution and incubated at 37°. Bacteria are counted after 0, 3, 24 and 48 hours. No bacteria are found in the cultures after cultivating during 3 hours which indicates that all bacteria were dead.

Example 13

The following bacterial strains are used:
*Helicobacter pylori* NCTC 11736, International reference strain
*Helicobacter pylori* S-3, isolated in Orebro, Sweden
*Helicobacter pylori* S-6, isolated in Orebro, Sweden
*Helicobacter pylori* F-6, isolated in Helsinki, Finland
*Helicobacter pylori* 7-88, isolated in Helsinki, Finland
*Campylobacter jejuni* S-562, isolated in Orebro, Sweden
*Campylobacter jejuni* S-261, isolated in Orebro, Sweden
*Staphylococcus epidermidis*, laboratory stock strain
*Streptococcus agalactiae*, group B, laboratory stock strain Helicobacters and campylobacters are two important intestinal pathogenic bacteria that cause gastroenteritis. *Helicobacter pylori* is especially recognized as the cause of intestinal infections and the causal agent in peptic ulcer diseases. The Staphylococcus strain is a common hospital bacterial species, and *Streptococcus agalactiae* is a vaginal bacterium causing abortion. There is a great demand for an antibacterial therapy, without side effects, that could be used as a broad spectrum antibiotic on the above bacteria. Presently, the treatment comprises bismuth combined with two different antibiotics.

The strains used in the tests are cultured overnight in enriched Mueller Hinton Broth. Colony-forming units (CFU) are in the range of $1 \times 10^6$/ml to $8 \times 10^7$/ml for *H. pylori* and $2 \times 10^7$/ml to $5 \times 10^8$/ml for *S. agalactiae* and *S. epidermidis*, respectively.

A volume of 0.1 ml is taken from each broth culture and mixed with 0.9 ml of the resultant propolis solutions of examples 3 and 5, and are incubated at 37° C. From each of these mixtures after 0, 3, 24 and 48 hours, 0.1 ml is taken and cultured on blood agar medium.

No growth of bacteria occurs after 3 hours, which indicates that the tested bacteria are killed after 3 hours of incubation in the examined solutions. Each of these tests is repeated at least twice, with the same results.

Example 14

The immunostimulating effect of the mixture according to the invention has been tested directly on cells from thymus and spleen (B- and T-lymphocytes and natural killer cells (NK cells)). In these tests, the mixture showed potent immunostimulating effects. The results of in vivo treatment are shown in FIG. 34. The composition according to the invention has also been given to animals in their feed, giving rise to increased activity of T- and B-cells in both thymus and spleen. The composition according to the invention increases both the humoral and cell mediated immune response.

In mice infected with Coxsackievirus B3 (CB3), the lifetime of the mice was significantly prolonged for mice treated prophylactically with the composition. The results are shown in FIG. 35.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of inhibiting bacteria comprising applying a mixture comprising compounds, each compound of the general formula

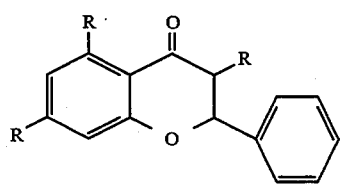

wherein each of the three R groups may be different from or the same as one or more of the other R groups, and each R group is selected from the group consisting of H, OH and

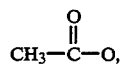

wherein the mixture is obtained by a process comprising ultrasonically treating an alcoholic solution of propolis to obtain an extract, and treating said extract with a salt solution to obtain a clear solution containing said compounds.

2. A method of inhibiting bacteria comprising applying a mixture of pinocembrin and pinobanksin-3-acetate as dominant detectable components of said mixture when said mixture is analyzed utilizing gas chromatography/mass spectrometry.

* * * * *